US011866480B2

(12) United States Patent
Hirsch et al.

(10) Patent No.: US 11,866,480 B2
(45) Date of Patent: Jan. 9, 2024

(54) VECTOR-MEDIATED IMMUNE TOLERANCE IN THE EYE

(71) Applicants: The University of North Carolina at Chapel Hill, Chapel Hill, NC (US); North Carolina State University, Raleigh, NC (US)

(72) Inventors: Matthew Louis Hirsch, Chapel Hill, NC (US); Brian Christopher Gilger, Raleigh, NC (US)

(73) Assignees: The University of North Carolina at Chapel Hill, Chapel Hill, NC (US); North Carolina State University, Raleigh, NC (US)

( * ) Notice: Subject to any disclaimer, the term of this patent is extended or adjusted under 35 U.S.C. 154(b) by 907 days.

(21) Appl. No.: 16/318,070

(22) PCT Filed: Jul. 26, 2017

(86) PCT No.: PCT/US2017/043831
§ 371 (c)(1),
(2) Date: Jan. 15, 2019

(87) PCT Pub. No.: WO2018/022683
PCT Pub. Date: Feb. 1, 2018

(65) Prior Publication Data
US 2021/0292388 A1    Sep. 23, 2021

Related U.S. Application Data

(60) Provisional application No. 62/366,822, filed on Jul. 26, 2016.

(51) Int. Cl.
| | |
|---|---|
| *C07K 14/705* | (2006.01) |
| *C07K 14/74* | (2006.01) |
| *A61P 27/02* | (2006.01) |
| *A61P 37/06* | (2006.01) |
| *A61K 9/00* | (2006.01) |
| *C12N 15/86* | (2006.01) |

(52) U.S. Cl.
CPC ...... *C07K 14/70539* (2013.01); *A61K 9/0048* (2013.01); *A61P 27/02* (2018.01); *A61P 37/06* (2018.01); *C12N 15/86* (2013.01); *C12N 2750/14142* (2013.01); *C12N 2750/14143* (2013.01); *C12N 2750/14171* (2013.01); *C12N 2830/50* (2013.01)

(58) Field of Classification Search
CPC .............................................. C07K 14/70539
See application file for complete search history.

(56) References Cited

U.S. PATENT DOCUMENTS

| | | | |
|---|---|---|---|
| 6,022,863 A | 2/2000 | Peyman | |
| 2003/0166277 A1 | 9/2003 | Zauderer et al. | |
| 2005/0014166 A1 | 1/2005 | Trono et al. | |
| 2005/0287129 A1 | 12/2005 | Cicciarelli et al. | |
| 2006/0188481 A1 | 8/2006 | Mori | |
| 2011/0135672 A1 | 6/2011 | Horuzsko et al. | |
| 2011/0274711 A1* | 11/2011 | Favier et al. ........ | A61K 38/17 424/192.1 |
| 2012/0177671 A1 | 7/2012 | Rulleau et al. | |
| 2014/0079688 A1 | 3/2014 | Sing | |

FOREIGN PATENT DOCUMENTS

| | | | |
|---|---|---|---|
| CN | 102076844 A | 5/2011 | |
| EP | 2264067 | 12/2010 | |
| FR | WO2014072534 A1 * | 5/2014 | .......... C07K 14/705 |
| WO | 2010/005527 | 1/2010 | |
| WO | 2013/138343 | 9/2013 | |
| WO | 2014/022423 | 2/2014 | |
| WO | 2016094679 A1 | 6/2016 | |

OTHER PUBLICATIONS

Bainbridge et al. (2001) "HLA-G remains a mystery" Trends in Immunology, vol. 22, No. 10, pp. 548-552. (Year: 2001).*
GenBank BC021708.2, Dec. 17, 2007, *Homo sapiens* major histocompatibility complex, class I, G, mRNA, available online: https://www.ncbi.nlm.nih.gov/nuccore/BC021708. (Year: 2007).*
Boura et al. (2014) "Evaluation of gene delivery strategies to efficiently overexpress functional HLA-G on human bone marrow stromal cells" Molecular Therapy-Methods & Clinical Development, 1, 14041, 10 pages. (Year: 2014).*
Kim et al. (1997) "Codon optimization for high-level expression of human erythropoietin (EPO) in mammalian cells" Gene, 199(1-2), 293-301. (Year: 1997).*
International Preliminary Report on Patentability corresponding to International Application No. PCT/US2017/043831 dated Feb. 7, 2019.
"Examination Report corresponding to European Application No. 17835156.5 dated May 21, 2021".
Forte et al. "Porcine Aortic Endothelial Cells Transfected with HLA-G are Partially Protected from Xenogeneic Human NK Cytotoxicity", Human Immunology 61(11):1066-1073 (2000).
Zhao et al. "Heterologous expression of mutated HLA-G decreases immunogenicity of human embryonic stem cells and their epidermal derivatives", Stem Cell Research 13(2):342-354 (2014).
von Websky et al. "Recombinant HLA-G as Tolerogenic Immunomodulant in Experimental Small Bowel Transplantation", PLOS One 11(7) e0158907 (2016) (16 pages).
LeMaoult et al. "Synthetic HLA-G proteins for therapeutic use in transplantation", The FASEB Journal 27(9):3643-3651 (2013).

(Continued)

*Primary Examiner* — James D Schultz
*Assistant Examiner* — James Joseph Graber
(74) *Attorney, Agent, or Firm* — Myers Bigel, P.A.

(57) ABSTRACT

This invention relates to vectors for delivery of human leukocyte antigen G to the eye and/or to cornea explants and methods of using the same for treatment and/or prevention of corneal transplant rejection and other disorders associated with an immune response and/or vascularization.

18 Claims, 16 Drawing Sheets

Specification includes a Sequence Listing.

(56) References Cited

OTHER PUBLICATIONS

Rebmann et al. "HLA-G as a Tolerogenic Molecule in Transplantation and Pregnancy", J. Immunology Research 2014:1-16 (2014).
Vance et ai. "AAV Gene Therapy for MPS1-associated Corneal Blindness", Scientific Reports 6(1):1-10 (2016).
Extended European Search Report corresponding to European Application No. 17835156.5 dated Jan. 29, 2020.
Kim et al. "Codon optimization for high-level expression of human erythropoietin (EPO) in mammalian cells", Gene 199:293-301 (1997).
Database GenBank: HZ285496.1 Nov. 26, 2015.
Grimm et al. "Novel Tools for Production and Purification of Recombinant Adenoassociated Virus Vectors", Human Gene Therapy 9:2745-2760 (1998).
Kapturczak et al. "Adeno-Associated Virus (AAV) as a Vehicle for Therapeutic Gene Delivery: Improvements in Vector Design and Viral Production Enhance Potential to Prolong Graft Survival in Pancreatic Islet Cell Transplantation for the Reversal of Type 1 Diabetes", Current Molecular Medicine 1:245-258 (2001).
International Search Report and Written Opinion corresponding to International Application No. PCT/US2017/043831 dated Nov. 2, 2017.
"Office Action corresponding to Israeli Application No. 263782 dated Jul. 14, 2022".
"Office Action corresponding to Chinese Application No. 201780049218.8 dated Nov. 3, 2022".
"Office Action corresponding to Canadian Application No. 3,028,786 dated Jun. 16, 2023".
"Full English of Office Action corresponding to Chinese Application No. 201780049218.8 dated Jul. 28, 2023".
Mauro et al. "A critical analysis of codon optimization in human therapeutics" Trends in Molecular Medicine, 20(11):604-613 (2014).
Office Action corresponding to Israeli Application No. 263,782 dated Jul. 27, 2023.
Office Action with partial English translation corresponding to Chinese Application No. 201780049218.8 dated Jul. 28, 2023.
"Examination Report corresponding to European Application No. 17835156.5 dated Apr. 19, 2023".
"Office Action corresponding to Chinese Application No. 201780049218.8 dated Nov. 14, 2023".

* cited by examiner

DAY 0

DAY 10

```
SEQUENCE LISTING

<160> NUMBER OF SEQ ID NOS: 4

<210> SEQ ID NO 1
<211> LENGTH: 1017
<212> TYPE: DNA
<213> ORGANISM: Artificial Sequence
<220> FEATURE:
<223> OTHER INFORMATION: Codon Optimized HLA-G1

<400> SEQUENCE: 1
atggtcgtga tggctcctcg cacactgttc ctgctgctgt ctggggctct gacactgact        60
gaaacttggg ctggatcaca ctcaatgaga tacttcagcg ccgccgtgag caggccatcc       120
cgcggcgagc ccaggtttat cgctatgggc tatgtggacg ataccagtt cgtgcgcttt        180 gactccgatt ctgcctgccc taggatggag cctcgcgccc cctgggtgga gagggagggc       240
ccagagtact gggaggagga gacccgcaac acaaaggccc acgcccagac cgaccggatg       300
aacctgcaga cactgagagg ctactataat cagtccgagg ccagctccca caccctgcag       360
tggatgatcg gctgtgacct gggctctgat ggccggctgc tgagaggcta cgagcagtac       420
gcctatgacg gcaaggatta tctggccctg aatgaggacc tgcggtcttg gaccgcagca       480
gatacagcag cccagatcag caagagaaag tgcgaggcag caaacgtggc agagcagagg       540
agagcatacc tggagggaac ctgcgtggag tggctgcacc ggtatctgga gaatggcaag       600
gagatgctgc agagagccga cccccctaag acccacgtga cacaccaccc agtgttcgat       660
tacgaggcca cactgaggtg ctgggcactg ggcttttatc ctgccgagat catcctgacc       720
tggcagcgcg acggcgagga tcagacacag gacgtggagc tggtggagac caagccagca       780
ggcgatggca cattccagaa gtgggcagca gtggtggtgc cttccggaga ggagcagcgg       840
tatacctgtc acgtgcagca cgagggactg ccagagccac tgatgctgag gtggaagcag       900
```

-continued

| tctagcctgc ccacaatccc tatcatgggc atcgtggccg gcctggtggt gctggccgcc | 960 |
| gtcgtcactg gggcagccgt ggcagccgtc ctgtggcgga aaaagtcatc tgattga | 1017 |

<210> SEQ ID NO 2
<211> LENGTH: 1140
<212> TYPE: DNA
<213> ORGANISM: Artificial Sequence
<220> FEATURE:
<223> OTHER INFORMATION: Codon Optimized HLA-G1

<400> SEQUENCE: 2

| atggttgtta tggctccgcg gacactgttc cttttgcttt ccggtgccct gacgctgact | 60 |
| gaaacgtggg cgggcagcca ctcaatgcgc tattttttcag ccgccgtttc acggccatca | 120 |
| cgcggagaac ctagattcat cgcaatgggg tatgtcgatg atactcagtt tgtaagattc | 180 |
| gactcagatt ccgcatgccc gcgcatggag cctcgcgctc cttgggttga gcgggaaggt | 240 |
| ccggaatact gggaggagga aacgaggaat accaaagctc acgctcagac agaccgaatg | 300 |
| aacctccaga cactccgagg ctattataac agagcgagg cctcctctca caccctgcag | 360 |
| tggatgattg ggtgcgatct gggtagtgat ggacgcttgc ttcgggggta tgaacagtac | 420 |
| gcctacgatg gaaaggatta tctggcccctt aatgaggact tgagatcctg gacggctgca | 480 |
| gatacagcag ctcaaatttc taagcgcaaa tgtgaagcgg ccaacgtcgc cgagcagaga | 540 |
| cgcgcctatc tggagggcac ttgcgtagag tggcttcacc gctaccttga aaatggaaaa | 600 |
| gagatgttgc agcgagcgga ccccccaaaa acccacgtta cccaccatcc tgtcttcgat | 660 |
| tatgaggcca cactcagatg ctgggcactg gttttttatc ctgcagaaat tattctgacc | 720 |
| tggcaaaggg acggcgagga ccagactcaa gatgtggagc ttgtagagac taagcccgca | 780 |
| ggggacggga cttttcaaaa gtgggctgct gtggtagtgc ccagtggaga ggaacagcga | 840 |
| tacacgtgtc atgttcaaca cgaaggattg cccgagccat tgatgttgag atggaagcaa | 900 |
| agttcactgc ccactatacc catcatggga atcgttgcgg gcttggtagt tcttgcggcc | 960 |
| gtcgtaacgg tgccgcagt ggcagcgtg ctctggcgga aaaaatcctc agacatcagt | 1020 |
| tctggaccag cgagctgtgc tgcgactcgt ggcgtaatca tggtcatagc tgtttcctgt | 1080 |
| gtgaaattgt tatccgctca caattccaca acaatacga gccggaagca taagtgtaa | 1140 |

<210> SEQ ID NO 3
<211> LENGTH: 966
<212> TYPE: DNA
<213> ORGANISM: Artificial Sequence
<220> FEATURE:
<223> OTHER INFORMATION: HLA-G5

<400> SEQUENCE: 3

| atggtcgtga tggctcctcg cacactgttc ctgctgctgt ctggggctct gacactgact | 60 |
| gaaacttggg ctggatcaca ctcaatgaga tacttcagcg ccgccgtgag caggccatcc | 120 |
| cgcggcgagc ccaggtttat cgctatgggc tatgtggacg ataccccagtt cgtgcgcttt | 180 |
| gactccgatt ctgcctgccc taggatggag cctcgcgccc cctgggtgga gagggagggc | 240 |
| ccagagtact gggaggagga gacccgcaac acaaaggccc acgcccagac cgaccggatg | 300 |
| aacctgcaga cactgagagg ctactataat cagtccgagg ccagctccca caccctgcag | 360 |
| tggatgatcg ctgtgaccct gggctctgat ggcggctgc tgagaggcta cgagcagtac | 420 |
| gcctatgacg gcaaggatta tctggccctg aatgaggacc tgcggtcttg gaccgcagca | 480 |

```
gatacagcag cccagatcag caagagaaag tgcgaggcag caaacgtggc agagcagagg        540
agagcatacc tggagggaac ctgcgtggag tggctgcacc ggtatctgga gaatggcaag        600
gagatgctgc agagagccga ccccctaag acccacgtga cacaccaccc agtgttcgat         660
tacgaggcca cactgaggtg ctgggcactg ggcttttatc ctgccgagat catcctgacc        720
tggcagcgcg acggcgagga tcagacacag gacgtggagc tggtggagac caagccagca       780
ggcgatggca cattccagaa gtgggcagca gtggtggtgc cttccggaga ggagcagcgg       840
tatacctgtc acgtgcagca cgagggactg ccagagccac tgatgctgag gtggaagcag       900
tctagcctgc ccacaatccc tatcatgggc atcgtggccg gcctggtggt gctggccgcc       960
gtcgtc                                                                  966

<210> SEQ ID NO 4
<211> LENGTH: 1074
<212> TYPE: DNA
<213> ORGANISM: Homo sapiens

<400> SEQUENCE: 4
atgccaactt tgtacaaaaa agttggcatg gtggtcatgg caccccgaac cctcttcctg        60
ctactctcgg gggccctgac cctgaccgag acctgggcgg gctcccactc catgaggtat       120
ttcagcgccg ccgtgtcccg gcccagccgc ggggagcccc gcttcatcgc catgggctac       180
gtggacgaca cgcagttcgt gcggttcgac agcgactcgg cgtgtccgag gatggagccg       240
cgggcgccgt gggtggagcg ggaggggcca gagtattggg aagaggagac acggaacacc       300
aaggcccacg cacagactga cagaatgaac ctgcagaccc tgcgcggcta ctacaaccag       360
agcgaggcca gttctcatac cctccagtgg atgattggct gcgacctggg gtccgacgga       420
cgcctcctcc gcgggtatga acagtatgcc tacgatggca aggattacct cgccctgaac       480
gaggacctgc gctcctggac cgcagcggac actgcggctc agatctccaa gcgcaagtgt       540
gaggcggcca atgtggctga acaaaggaga gcctacctgg agggcacgtg cgtggagtgg       600
ctccacagat acctggagaa cgggaaggag atgctgcagc gcgcggaccc ccccaagaca       660
cacgtgaccc accaccctgt ctttgactat gaggccaccc tgaggtgctg ggccctgggc       720
ttctaccctg cggagatcat actgacctgg cagcgggatg gggaggacca gacccaggac       780
gtggagctcg tggagaccaa gcctgcaggg gatggaacct tccagaagtg ggcagctgtg       840
gtggtgcctt ctggagagga gcagagatac acgtgccatg tgcagcatga ggggctgccg       900
gagcccctca tgctgagatg aagcagtct tccctgccca ccatccccat catgggtatc        960
gttgctggtc tggttgtcct tgcagctgta gtcactggag ctgcggtcgc tgctgtgctg      1020
tggaggaaga gagctcaga tgcccaactt tcttgtacaa agttggcatt ataa             1074
```

VECTOR-MEDIATED IMMUNE TOLERANCE IN THE EYE

STATEMENT OF PRIORITY

This application is a 35 U.S.C. § 371 national phase application of PCT Application PCT/US2017/043831 filed Jul. 26, 2017, which claims the benefit of U.S. Provisional Application Ser. No. 62/366,822, filed Jul. 26, 2016, the entire contents of each of which are incorporated by reference herein in its entirety.

STATEMENT OF GOVERNMENT SUPPORT

This invention was made with government support under Grant Nos. AI072176 and AR064369 awarded by the National Institutes of Health. The government has certain rights to this invention.

STATEMENT REGARDING ELECTRONIC FILING OF A SEQUENCE LISTING

A Sequence Listing in ASCII text format, submitted under 37 C.F.R. § 1.821, entitled ASTR-001-01US-Sequence-listing, 6.18 KB in size, generated Dec. 15, 2022, and filed via EFS-Web, is provided in lieu of a paper copy. This Sequence Listing is hereby incorporated by reference into the specification for its disclosures.

FIELD OF THE INVENTION

This invention relates to vectors for delivery of human leukocyte antigen G (HLA-G) to the eye and/or to cornea explants and methods of using the same for treatment and/or prevention of corneal transplant rejection and other disorders associated with an immune response and/or vascularization.

BACKGROUND OF THE INVENTION

Corneal engraftment to treat vision loss is the most common form of tissue transplantation worldwide with approximately 47,000 occurring in the United States alone. In low risk patients, transplant rejection after two years is approximately 15%, the success of which is largely due to the lack of vascularization in relatively healthy corneas. In contrast, high risk corneal transplants demonstrate an alarming 50-70% rejection rate after only two years, and many patients with severe corneal disease are not considered candidates for the procedure. These high risk cases are defined as having a significant amount of pre-existing corneal vascularization and/or having a prior engraftment. Current treatments rely in part on topical and systemic corticosteroids that exhibit low levels of success and serious adverse side effects.

The eye is widely considered an immune privileged site and the designation includes the cornea. The immune privileged status of the cornea is maintained by several mechanisms including the blood-ocular barrier, a lack of corneal lymphatics and vasculature, the expression of Fas ligand on corneal cells, low expression of major histocompatibility complex (MHC) class I and II molecules on corneal cells, few mature antigen presenting cells (APCs) in the central cornea, presence of immunomodulatory factors in the aqueous humor and tear film (e.g., alpha melanocyte stimulating hormone and transforming growth factor beta), and the phenomenon of anterior chamber associated immune deviation. Corneal grafts are considered at high risk for rejection when there is a loss of any component of corneal immune privilege, which may occur with ocular inflammation, infection, trauma, and subsequent vascularization.

Corneal graft rejection develops within weeks after surgery and is manifested clinically by an epithelial or endothelial rejection line, stromal rejection band, increased corneal thickness, and anterior segment inflammation (keratic precipitates, aqueous flare, and cells). With this acute graft rejection, donor MHC molecules (class I and II) on the surface of donor APCs are recognized directly by host recipient T cells resulting in rapid effector inflammation, and have been described as the direct pathway for graft rejection. As time after grafting increases and donor APCs migrate out of the donor tissue, it becomes less likely that this type of rejection will develop. Chronically, however, graft failure can also occur when donor MHC molecules are taken up and presented by recipient MHC molecules to recipient T cells, initiating the afferent immunologic response, which is referred to as the indirect pathway of graft rejection. Thus, recipient T-cell recognition of MHC alloantigens plays an important role in corneal graft rejection.

Donor class I antigens (HLA-A, B, C of epithelium, stromal, and endothelial cells) get recognized by host cytotoxic T cells (CD8$^+$) while donor class II antigens presented by APCs (e.g., lymphocytes, macrophages, Langerhans cells, and interstitial dendritic cells) get recognized by helper T cells (CD4$^+$), which when activated upregulate chemokines, cytokines (IL-2, IFN-gamma, macrophage activation factor, migration inhibition factor) and toxic molecules including nitric oxide, superoxide radicals, and tumor necrosis factor alpha), each which damage the corneal allograft. These cytokines and chemokines enhance inflammation by further expression of class II antigens. Cytotoxic T lymphocytes (CTLs) are the primary effector cells which directly attack cells bearing the foreign antigen. In addition to the adaptive immune response, NK cells and macrophages of the innate immune response may also play a role in corneal graft rejection. Long-term survival of corneal grafts is dependent on the development of CD4$^+$ CD25$^+$ Foxp3$^+$ regulatory T-cells that have a high expression of Foxp3$^+$ and are effective in suppression of T cell proliferation.

Other than direct recognition and lysis by CTLs, another primary, yet indirect, factor in corneal graft rejection is the vascularization and lymphatics in recipient corneas; the presence of either of which abolishes corneal immune privilege. Clinically, it is observed that the initial location of rejection is at the corneal graft margin nearest to host vascularization. Blood and lymph vessels enhance graft rejection by providing a direct route for egression of alloantigens (blood vessels) or APCs (lymph) to the peripheral immune system and lymph nodes and also by facilitating the migration of circulating effector immune cells and alloantigen-specific T cells to the corneal allograft to initiate rejection.

The present invention overcomes shortcomings in the art by providing vectors for expression of HLA-G in corneal explants and in the eye and methods for treating and/or preventing corneal transplant rejection and other eye disorders associated with an immune response and/or vascularization.

SUMMARY OF THE INVENTION

This invention is based on the concept of mimicking the body's natural method of immune tolerance to foreign tissue via gene delivery of the human leukocyte antigen G (HLA- G). Both soluble and transmembrane forms of HLA-G are expressed at the maternal/fetal interface to prevent rejection of the fetus, which expresses foreign antigens. The effects of HLA-G are at multiple levels including anti-vascularization and direct interactions with T cells and antigen presenting cells.

HLA-G expression in the cornea may improve tolerance of donor corneal graft antigens, in part, through its ability to inhibit NK cells, effector cytotoxic T cells, T cell proliferation, and donor antigen presentation. In addition to the ability of HLA-G to inhibit CTLs, the transmembrane and soluble forms of HLA-G inhibit angiogenesis and trigger apoptosis of endothelial cells. Thus, HLA-G expression may improve corneal graft tolerance indirectly through prevention/reduction of corneal vascularization and/or directly via CTL inactivation.

The ability of HLA-G to inhibit vascularization and suppress the immune response in corneal explants and in the eye leads to the treatment and/or prevention of transplant rejection and other eye disorders associated with an immune response and/or vascularization.

Thus, one aspect of the invention relates to a polynucleotide encoding HLA-G, wherein the nucleotide sequence has been codon-optimized for expression in human cells.

Another aspect of the invention relates to an AAV vector genome comprising the nucleic acid of the invention, an AAV particle comprising the AAV vector genome, and a pharmaceutical composition comprising the AAV particle.

A further aspect of the invention relates to an expression cassette comprising at least one polynucleotide encoding HLA-G and vectors, viral particles, cells, transgenic animals, and pharmaceutical compositions comprising the same.

An additional aspect of the invention relates to a method of producing a recombinant AAV particle, comprising providing to a cell permissive for AAV replication: (a) recombinant AAV template comprising (i) the polynucleotide or the expression cassette of the invention, and (ii) an inverted terminal repeat (ITR); and (b) a polynucleotide comprising Rep coding sequences and Cap coding sequences; under conditions sufficient for the replication and packaging of the recombinant AAV template; whereby recombinant AAV particles are produced in the cell.

Another aspect of the invention relates to a method of delivering HLA-G to a cell, comprising contacting the cell with the recombinant AAV particle or the pharmaceutical composition of the invention, thereby delivering HLA-G to the cell.

Another aspect of the invention relates to a method of expressing HLA-G in a cell, comprising contacting the cell with the recombinant AAV particle or the pharmaceutical composition of the invention, thereby expressing HLA-G in the cell.

A further aspect of the invention relates to a method of delivering HLA-G to a cornea explant, comprising contacting the cornea explant with the recombinant AAV particle or the pharmaceutical composition of the invention, thereby delivering HLA-G to the cornea explant.

An additional aspect of the invention relates to a method of inhibiting rejection of a cornea explant after transplantation in a mammalian subject, comprising contacting the cornea explant with the recombinant AAV particle or the pharmaceutical composition of the invention (e.g., before, during, and/or after transplantation), thereby inhibiting rejection of the cornea explant after transplantation.

Another aspect of the invention relates to a method of administering/delivering HLA-G to the eye of a mammalian subject, comprising administering to the eye of the mammalian subject a cell that has been contacted with the recombinant AAV particle or the pharmaceutical composition of the invention, thereby administering HLA-G to the eye of the mammalian subject.

Another aspect of the invention relates to a method of administering/delivering HLA-G to the eye of a mammalian subject, comprising administering to the eye of the mammalian subject the recombinant AAV particle or the pharmaceutical composition of the invention, thereby administering HLA-G to the eye of the mammalian subject.

A further aspect of the invention relates to a method of treating an eye disorder associated with an immune response and/or vascularization in a mammalian subject (e.g., a subject in need thereof), comprising administering/delivering to the eye of the mammalian subject a cell that has been contacted with (e.g., a cell that comprises) the recombinant AAV particle or the pharmaceutical composition of the invention, thereby treating the eye disorder associated with an immune response and/or vascularization.

An additional aspect of the invention relates to a method of treating an eye disorder associated with an immune response and/or vascularization in a mammalian subject in need thereof, comprising administering to the eye of the mammalian subject the recombinant AAV particle or the pharmaceutical composition of the invention, thereby treating the eye disorder associated with an immune response and/or vascularization.

These and other aspects of the invention are set forth in more detail in the description of the invention below.

DETAILED DESCRIPTION OF THE INVENTION

Figure 1A:
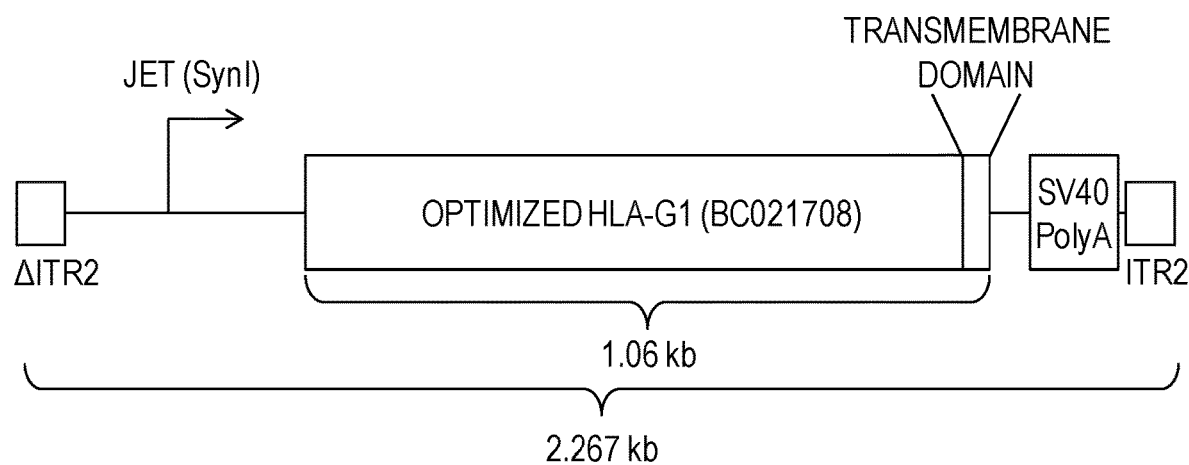
FIGS. 1A-1C shows characterization of scAAV8G9-optHLA-G in vitro. A) A cartoon of the self-complementary scAAV8G9-optHLA-G vector cassette. B) Confirmation of optHLA-G isoform production in 293 cells by Western blot. JEG-3 cells are placental cells and serve as a positive control. Western blot images have been cropped and aligned to concisely represent these data and full-length blots are presented in FIG. 11. C) Diaminobenzidine staining of optHLA-G isoforms, imaged at the same exposure times, following transfection of 293 cells with the indicated cDNAs. ITR=inverted terminal repeat.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *Patent In User Manual,* 99-102 (November 1990) (U.S. Patent and Trademark Office).

Except as otherwise indicated, standard methods known to those skilled in the art may be used for the construction of recombinant parvovirus and AAV (rAAV) constructs, packaging vectors expressing the parvovirus Rep and/or Cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, N.Y., 1989); AUSUBEL et al., CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

Definitions

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention (e.g., rAAV replication). Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in enzymatic activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al., VIROLOGY, volume 2, chapter 69 (4th ed., Lippincott-Raven Publishers). A number of relatively new AAV serotypes and clades have been identified (See, e.g., Gao et al., (2004) *J. Virol.* 78:6381; Moris et al., (2004) *Virol.* 33-:375; and Table 1).

The parvovirus vectors, particles, and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC 001401, NC 001729, NC 001863, NC 001829, NC 001862, NC 000883, NC 001701, NC 001510, NC 006152, NC 006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J Virol.* 71:6823; Chiorini et al., (1999) *J Virol.* 73:1309; Gao et al., (2002) *Proc. Nat. Acad. Sci. USA* 99:11854; Moris et al., (2004) *Virol.* 33-:375-383; Mori et al., (2004) *Virol.* 330: 375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, Pa. (incorporated herein in its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

|  | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |

|  | GenBank Accession Number |
|---|---|
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

As used herein, "transduction" of a cell by parvovirus or AAV refers to parvovirus/AAV-mediated transfer of genetic material into the cell. See, e.g., FIELDS et al., VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), and can be either single or double stranded DNA sequences.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351 (1987); the method is similar to that described by Higgins & Sharp, CABIOS 5:151 (1989).

Another example of a useful algorithm is the BLAST algorithm, described in Altschul et al., J Mol. Biol. 215:403 (1990) and Karlin et al., Proc. Natl. Acad. Sci. USA 90:5873 (1993). A particularly useful BLAST program is the WU-BLAST-2 program which was obtained from Altschul et al., Meth. Enzymol., 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., Nucleic Acids Res. 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. In some embodiments, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone or a plasmid.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) Curr. Topics Microbiol. Immunol. 158: 97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) Mol. Therapy 2:619.

Further, the viral capsid or genomic elements can contain other modifications, including insertions, deletions and/or substitutions.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

The term "codon-optimized," as used herein, refers to a gene coding sequence that has been optimized to increase expression by substituting one or more codons normally present in a coding sequence (for example, in a wild-type sequence, including, e.g., a coding sequence for HLA-G) with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wild-type gene in an otherwise similar cell.

Vectors Expressing HLA-G

The ability of HLA-G to inhibit vascularization and suppress the immune response in corneal explants and in the eye leads to the treatment and/or prevention of transplant rejection in the eye and other eye disorders associated with an immune response and/or vascularization.

One aspect of the invention relates to a polynucleotide encoding human leukocyte antigen-G (HLA-G), wherein the nucleotide sequence has been codon-optimized for expression in human cells. In certain embodiments, the polynucleotide encodes the transmembrane form of HLA-G (HLA-G1) and/or the soluble form of HLA-G (HLA-G5). In some embodiments, the nucleic acid comprises a nucleotide sequence that is at least 80% identical to SEQ ID NO:1 or SEQ ID NO: 2 or a fragment thereof that encodes a functional HLA-G polypeptide, e.g., at least 60%, 65%, 70%, 75%, 80%, 85%, 90%, 91%, 92%, 93%, 94%, 95%, 96%, 97%, 98%, or 99% identical to SEQ ID NO:1 or SEQ ID NO: 2. In some embodiments, the nucleic acid comprises, consists essentially of, or consists of the nucleotide sequence of SEQ ID NO:1 or SEQ ID NO: 2 or a fragment thereof that encodes a functional HLA-G polypeptide. As used herein, a functional HLA-G polypeptide is a portion of the full length HLA-G polypeptide that retains at least about 25%, 50%, or 75% of the biological activity of full length HLA-G, e.g., the immunosuppressant and/or antivascular activity. The polynucleotide fragment that encodes a functional HLA-G polypeptide may comprise contiguous and/or non-contiguous deletions of nucleotides of the wild-type nucleotide sequence.

Methods of codon optimizing a nucleotide sequence to maximize expression in an organism are well known in the art and can be carried out using software available to the public. The wild-type nucleotide sequence of HLA-G is known in the art and described herein as SEQ ID NO:4.

In some embodiments, the codon-optimized sequences of the invention provide enhanced expression of HLA-G in human cells relative to the wild-type sequence, e.g., at least about a 2-fold, 3-fold, 4-fold, or 5-fold increase in expression or at least about 10%, 20%, 30%, 40%, 50%, 60%, 70%, 80%, 90%, 100%, 150%, 200%, or 300% enhancement of expression relative to the wild-type sequence.

The invention also provides an expression cassette comprising at least one polynucleotide encoding HLA-G. In certain embodiments, the HLA-G polynucleotide is a wild-type HLA-G sequence or a codon-optimized sequence. The expression cassette may comprise a polynucleotide encoding HLA-G1, a polynucleotide encoding HLA-G5, or both. In certain embodiments, the expression cassette comprises a single open reading frame that alternatively expresses HLA-G1 or HLA-G5. The alternative expression may be due to differential splicing, e.g., due to the presence of intron donor/acceptor sites, e.g., surrounding the nucleotides encoding the transmembrane portion of HLA-G. Naturally, HLA-G1 and HLA-G5 are produced by differential splicing that terminates HLA-G5 prior to the ~25 amino acid transmembrane domain at the C-terminus of HLA-G1. In this embodiment, a controllable synthetic intron that allows splicing to two different exons may be used to produce HLA-G1 and HLA-G5 from the same promoter.

The expression cassette may further comprise additional expression control elements, e.g., a promoter, enhancer, and/or polyadenylation signal. In some embodiments, the promoter may be a constitutive promoter, e.g., a CMV promoter. In other embodiments, the promoter may be a tissue-specific or preferred promoter or a cell type-specific or preferred promoter. In some embodiments, the promoter may be a cornea-specific promoter, e.g., keratocan. If the expression cassette comprises more than one HLA-G open reading frame, in some embodiments, each open reading frame may be operably linked to one or more expression control elements. In other embodiments, multiple HLA-G open reading frames may be operably linked to a single expression control element such as a promoter.

In some embodiments, the expression vector may be part of a viral vector genome, e.g., a parvovirus vector genome, e.g., an adeno-associated virus (AAV) vector genome. In certain embodiments, the expression cassette further comprises at least one AAV inverted terminal repeat (ITR), e.g., two AAV ITRs. The two ITRs may have the same nucleotide sequence or different nucleotide sequences. The AAV ITRs may be from any AAV serotype, e.g., AAV2. Each ITR independently may be the wild-type sequence or a modified sequence. In some embodiments, the expression cassette is an AAV genome, e.g., a self-complementary AAV genome.

Another aspect of the invention relates to a vector comprising the polynucleotides or expression cassettes of the invention. Suitable vectors include, but are not limited to, a plasmid, phage, viral vector (e.g., an AAV vector, an adenovirus vector, a herpesvirus vector, an alphavirus, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat). In some embodiments, the vector is a viral vector, e.g., a parvovirus vector, e.g., an AAV vector, e.g., an AAV8 or AAV9 vector. The viral vector may further comprise a nucleic acid comprising a recombinant viral template, wherein the nucleic acid is encapsidated by the parvovirus capsid. The invention further provides a recombinant parvovirus particle (e.g., a recombinant AAV particle) comprising the polynucleotides of the invention. Viral vectors and viral particles are discussed further below.

In certain embodiments, the viral vector exhibits a modified tropism due to the presence of the capsid protein of the invention. In one embodiment, the parvovirus vector exhibits systemic tropism for the cornea and/or another tissue of the eye. In other embodiments, the parvovirus vector has reduced tropism for liver compared to a virus vector comprising a wild-type capsid protein.

An additional aspect of the invention relates to a transformed cell comprising the polynucleotide, expression cassette, and/or vector of the invention. In some embodiments, the polynucleotide, expression cassette, and/or vector is stably incorporated into the cell genome.

Another aspect of the invention relates to a transgenic animal comprising the polynucleotide, expression cassette, vector, and/or the transformed cell of the invention.

A further aspect of the invention relates to a pharmaceutical formulation comprising the polynucleotide, expression cassette, vector, and/or transformed cell of the invention in a pharmaceutically acceptable carrier.

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) the polynucleotide or expression cassette of the invention, and (ii) a parvovirus ITR; (b) a polynucleotide comprising Rep and Cap coding sequences; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

In some embodiments, the recombinant parvovirus template comprises an ITR that is not resolved by Rep to make duplexed AAV vectors as described in international patent publication WO 01/92551.

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can be collected from the medium and/or by lysing the cells.

The cell can be a cell that is permissive for parvoviral viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other Ela trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the parvovirus rep/cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In particular embodiments, the parvovirus template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the E1a or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can be provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by ITRs so that these sequences are not packaged into the parvovirus virions.

Zhang et al., ((2001) *Gene Ther.* 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and parvovirus template as described, for example, by Urabe et al., (2002) *Human Gene Ther.* 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al., (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of polynucleotides to cells in vitro, ex vivo, and in vivo. In particular, the virus vectors can be advantageously employed to deliver or transfer nucleic acids to animal, including mammalian, cells. In particular, the virus vectors of the present invention are useful for the delivery of a polynucleotide encoding HLA-G to the eye of a subject or to eye tissue intended for transplantation, e.g., corneal explants.

It will be understood by those skilled in the art that the polynucleotide encoding HLA-G can be operably associated with appropriate control sequences. For example, the polynucleotide can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the HLA-G polynucleotide sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the nucleic acid sequence. Inducible promoters/enhancer elements for gene delivery can be tissue-specific or -preferred promoter/enhancer elements, and include eye specific or preferred (including retina-specific and cornea-specific) promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the polynucleotide sequence is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors of the invention can be parvovirus vectors, e.g., AAV vectors. The AAV vectors may be any AAV serotype. In some embodiments, the AAV vector is an AAV2, AAV8, or AAV9 vector. In some embodiments, the AAV vector is a hybrid vector, e.g., one having a capsid protein from one serotype and a genome from another serotype or one having a synthetic capsid protein. In certain embodiments, the vector comprises a hybrid capsid with an altered tropism. In one example the hybrid capsid comprising a glycan binding site (e.g., a galactose binding site) from one serotype (e.g., AAV9) in a capsid sequence from another serotype (e.g., AAV8) (see, e.g., WO 2014/144229, incorporated by reference herein in its entirety).

The virus vectors according to the present invention provide a means for delivering HLA-G polynucleotide into a broad range of cells, including dividing and non-dividing cells. The virus vectors can be employed to deliver the polynucleotide to a cell in vitro, e.g., to produce a polypeptide in vitro or for ex vivo gene therapy. The virus vectors are additionally useful in a method of delivering the polynucleotide to a subject in need thereof, e.g., to express HLA-G. In this manner, the polypeptide can be produced in vivo in the subject. The subject can be in need of the polypeptide because the subject has a deficiency of the polypeptide. Further, the method can be practiced because the production of the polypeptide in the subject may impart some beneficial effect.

The virus vectors can also be used to produce HLA-G in cultured cells or in a subject (e.g., using the subject as a bioreactor to produce the polypeptide or to observe the effects of the polypeptide on the subject, for example, in connection with screening methods).

The virus vectors of the present invention can be employed to deliver a polynucleotide encoding HLA-G to treat and/or prevent any disease state or condition for which it is beneficial to deliver HLA-G, e.g., corneal transplant rejection, immune-mediated dry eye, allergic conjunctivitis, immune-mediated uveitis, or age-related macular degeneration/chronic neovascularization.

Virus vectors according to the instant invention find use in diagnostic and screening methods, whereby the HLA-G polynucleotide is transiently or stably expressed in a cell culture system, in an organ or organ culture (e.g., an eye), or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

Alternatively, the virus vector may be administered to a cell ex vivo and the altered cell is administered to the subject. The virus vector comprising the HLA-G polynucleotide is introduced into the cell, and the cell is administered to the subject, where the nucleic acid can be expressed.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults. In some embodiments, the subject is one in need of treatment, e.g., a subject that has been diagnosed with or is suspected of having a disorder treatable by the methods of the invention.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to cells of the eye (including retinal cells, retinal pigment epithelium, ciliary body epithelium, and corneal cells (e.g., keratocytes, epithelial cells, and endothelial cells)) and immune cells. In some embodiments, the cell is a cell to be delivered to the eye for expression of HLA-G, such as a stem cell, e.g., a mesenchymal stem cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

A further aspect of the invention is a method of administering the virus vector to subjects. Administration of the virus vectors according to the present invention to a human subject or an animal in need thereof can be by any means known in the art. Optionally, the virus vector is delivered in a treatment effective or prevention effective dose in a pharmaceutically acceptable carrier.

Dosages of the virus vector to be administered to a subject depend upon the mode of administration, the disease or condition to be treated and/or prevented, the individual subject's condition, the particular virus vector, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$ transducing units, optionally about $10^8$ to about $10^{15}$ or about $10^8$ to about $10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration to the eye include intrastromal, topical, intravitreal, intracameral, subconjunctival, subretinal, episcleral, intrascleral, periocular, suprachoroidal, retrobulbar, and any combination thereof.

Delivery to a target tissue can also be achieved by delivering a depot comprising the virus vector. In representative embodiments, a depot comprising the virus vector is implanted into the cornea or other tissue of the eye or the tissue can be contacted with a film or other matrix comprising the virus vector. Such implantable matrices or substrates are described in U.S. Pat. No. 7,201,898.

Thus, one aspect of the invention relates to a method of expressing HLA-G in a cell, comprising contacting the cell with the recombinant AAV particle or the pharmaceutical composition of the invention, thereby expressing HLA-G in the cell. In some embodiments, HLA-G1, HLA-G5, or both are expressed in the cell.

A further aspect of the invention relates to a method of delivering HLA-G to a cornea explant, comprising contacting the cornea explant with the recombinant AAV particle or the pharmaceutical composition of the invention, thereby delivering HLA-G to the cornea explant.

An additional aspect of the invention relates to a method of inhibiting rejection of a cornea explant after transplantation in a mammalian subject, comprising contacting the cornea explant with the recombinant AAV particle or the pharmaceutical composition of the invention, thereby inhibiting rejection of the cornea explant after transplantation. In some embodiments, the transplantation is an allogeneic transplantation. In some embodiments, the transplantation is a xenotransplantation. In some embodiments, the cornea explant is from a non-primate, e.g., a pig, and is transplanted to a primate, e.g., a human.

Another aspect of the invention relates to a method of carrying out a transplantation, e.g., a xenotransplantation, of a cornea explant, comprising contacting the cornea explant with the recombinant AAV particle or the pharmaceutical composition of the invention. In some embodiments, the cornea explant is from a primate, e.g., a human, and is transplanted to a primate, e.g., a human. In some embodiments, the cornea explant is from a non-primate, e.g., a pig, and is transplanted to a primate, e.g., a human.

In some embodiments, the cornea explant is contacted with the recombinant AAV particle or the pharmaceutical composition prior to transplantation. In some embodiments, the cornea explant is contacted with the recombinant AAV particle or the pharmaceutical composition during and/or after transplantation. In some embodiments, the cornea explant is contacted with the recombinant AAV particle or the pharmaceutical composition before, during, and/or after transplantation. The AAV particle or the pharmaceutical composition may be delivered to the explant by any means effective to express HLA-G in the explant. In some embodiments, the AAV particle or the pharmaceutical composition is injected into the explant. In some embodiments, the explant is incubated in the AAV particle or the pharmaceutical composition.

In some embodiments, HLA-G1, HLA-G5, or both are expressed in the cornea explant.

An additional aspect of the invention relates to a method of administering HLA-G to the eye of a mammalian subject, comprising administering to the eye of the mammalian subject a cell that has been contacted with the recombinant AAV particle or the pharmaceutical composition of the invention, thereby administering HLA-G to the eye of the mammalian subject. In some embodiments, the cell is a stem cell, e.g., a mesenchymal stem cell.

Another aspect of the invention relates to a method of administering HLA-G to the eye of a mammalian subject, comprising administering to the eye of the mammalian subject the recombinant AAV particle or the pharmaceutical composition of the invention, thereby administering HLA-G to the eye of the mammalian subject.

In some embodiments, HLA-G1, HLA-G5, or both are expressed in the eye or in a portion or tissue of the eye.

A further aspect of the invention relates to a method of treating an eye disorder associated with an immune response and/or vascularization in a mammalian subject in need thereof, comprising administering to the eye of the mammalian subject a cell that has been contacted with the recombinant AAV particle of the invention or the pharmaceutical composition of the invention, thereby treating the eye disorder associated with an immune response and/or vascularization. In some embodiments, the cell is a stem cell, e.g., a mesenchymal stem cell.

An additional aspect of the invention relates to a method of treating an eye disorder associated with an immune response and/or vascularization in a mammalian subject in need thereof, comprising administering to the eye of the mammalian subject the recombinant AAV particle of the invention or the pharmaceutical composition of the invention, thereby treating the eye disorder associated with an immune response and/or vascularization.

In some embodiments, HLA-G1, HLA-G5, or both are expressed in the eye or in a portion or tissue of the eye.

The AAV particle or pharmaceutical composition may be delivered to the eye or to a part of the eye by any means known in the art to be effective for delivery. In some embodiments, the AAV particle or pharmaceutical composition is administered by a route selected from the group consisting of intrastromal, topical, intravitreal, intracameral, subconjunctival, subretinal, episcleral, intrascleral, periocular, suprachoroidal, retrobulbar, and any combination thereof.

In some embodiments, the eye disorder associated with an immune response and/or vascularization is a disorder associated with an immune response. As used herein, a disorder associated with an immune response is a disorder in which a cellular and/or humoral immune response is a cause of one or more symptoms of the disorder and inhibition of the immune response results in an amelioration of one or more symptoms of the disorder. Examples include, without limitation, transplant rejection, immune-mediated dry eye, allergic conjunctivitis, and immune-mediated uveitis. HLA-G1 expression is associated with suppression of the immune response. Thus, treatment of an eye disorder associated with an immune response may be treated by expression of HLA-G1 or both HLA-G1 and HLA-G5.

In some embodiments, the eye disorder associated with an immune response and/or vascularization is a disorder associated with vascularization. As used herein, a disorder associated with vascularization is a disorder in which vascularization is a cause of one or more symptoms of the disorder and inhibition of vascularization results in an amelioration of one or more symptoms of the disorder. Examples include, without limitation, cornea trauma, age-related macular degeneration, diabetic retinopathy, vascularization in the posterior eye, choroidal neovascularization, and neovascular glaucoma. HLA-G5 expression is associated with suppression of vascularization. Thus, treatment of an eye disorder associated with vascularization may be treated by expression of HLA-G5 or both HLA-G5 and HLA-G1.

In some embodiments, the expression of HLA-G1 and HLA-G5 together is more effective than expression of other polypeptide alone, e.g., having an additive or synergistic effect.

Expression of both HLA-G1 and HLA-G5 in the eye or in an explant may be carried out using a single vector that expresses both polypeptides or using separate vectors each expressing one of the polypeptides. If using separate vectors, the vectors may be administered in the same composition of in separate compositions administered sequentially or at different times.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local manner, for example, in a depot or sustained-release formulation. Further, the virus vector and/or virus capsid can be delivered adhered to a surgically implantable matrix (e.g., as described in U.S. Patent Publication No. 2004-0013645).

Having described the present invention, the same will be explained in greater detail in the following examples, which are included herein for illustration purposes only, and which are not intended to be limiting to the invention.

Example 1

AAV Vector-Meditated Expression of HLA-G Reduces Injury-Induced Corneal Vascularization and Immune Cell Infiltration The purpose of this study was to engineer and validate a therapeutic, based on a natural mechanism of immune suppression, for the treatment of corneal vascularization following insult. Towards this end, HLA-G cDNA was enhanced by codon optimization and validated in a self-complementary AAV vector context in vitro. Then, the optimized HLA-G1 and 5 cassettes were packaged in a capsid proficient for multi-species cornea gene delivery (Vance et al., *Scientific Rep.* 6:22131 (2016)), and administered via intrastromal injection 8 days following a corneal chemical burn in a rabbit model. In contrast to the control injected corneas which became heavily vascularized, corneas that received scAAV8G9-optHLA-G demonstrated the near complete absence of vasculature over a 2-month period following the insult. This result was coupled with decreased immune cell infiltration of the cornea, which included cytotoxic T lymphocytes. Concerning biodistribution following intrastromal injection of traumatized cornea, although vector genomes were not detected outside the cornea, an AAV capsid neutralizing antibody response was elicited in approximately 50% of cases. The collective data demonstrate the clinical potential of scAAV8G9-optHLA-G to eliminate vascularization of the cornea while alluding to broader roles in ocular surface immunity and the possibility of allogeneic organ transplantation.

Materials and Methods

Optimized AAV HLA-G construct and in vitro expression: The HLA-G1 cDNA was codon optimized (GenScript USA, Piscataway, N.J.) and Western blot detection was used to compare the amount of plasmid-borne HLA-G1 from either WT or codon optimized HLA-G1 cDNA. Using PCR amplification, the transmembrane domain of HLA-G1 was then deleted to generate the soluble isoform, HLA-G5, cDNA. Following transfections of these plasmids in human embryonic kidney 293 cells, cell lysate was made and Western blot analysis was used to detect the size of the protein products that were generated. Immunocytochemistry, with the use of 3,3'-diaminobenzidine (DAB), was used to look at the intracellular localization of HLA-G1 and HLA-G5 in transfected 293 cells. Human placenta cells (JEG-3 cells) were used as a positive control (ATCC® HTB36™). Both HLA-G1 and HLA-G5 were then cloned into a self-complementary AAV plasmid context.

In vivo HLA-G expression following intrastromal injection of scAAV8G9-optHLA-G: The use of animals in this study was tightly adhered to the NIH Guide for the Care and Use of Laboratory Animals and the protocol was approved and monitored by the North Carolina State University Institutional Animal Use and Care committee (IACUC). Outbred normal male New Zealand White rabbits (*Oryctolagus cuniculus*) were used. With the rabbits anesthetized and following application of a topical anesthetic (0.5% proparacaine HCl [Alcaine, Alcon Laboratories, Fort Worth, Tex.]), a corneal wound was created in the right eye by applying a 5.0 mm-diameter circular filter disc that had been incubated in 20 µl of 1 M NaOH for 30 seconds to the central cornea (Wang et al., *Ophthalmic Res.* 46:66 (2011); Ye et al., *Eye* 20:482 (2006)). Seven days after corneal wounding, each rabbit was anesthetized and both eyes received an intrastromal injection with either saline solution (balanced salt solution (BSS), Alcon Laboratories, Fort Worth, Tex.), or scAAV8G9 vectors encoding for GFP, or at a 1:1 ratio, a combination of HLA-G1+HLA-G5 vectors (n=3 for each treatment group). For each injection, a 31-gauge needle was used to deliver 50 µL of either the saline solution or, at a viral concentration of $1\times10^9$ vg/µl, the AAV vectors into the superficial corneal stromal. Following wounding and after intrastromal injections, prophylactic antibiotics (Moxifloxacin, Alcon Laboratories, Fort Worth, Tex.) were applied topically to each cornea and buprenorphine was given subcutaneously to help reduce post-operative discomfort. Following the injections and while conscious, in vivo expression of GFP was evaluated in rabbits that were injected with scAAV8G9-GFP using a scanning laser ophthalmoscope (SLO) with a 482 nm laser source (Infrared cSLO; RetiMap Roland Consult, Germany, Wiesbaden, Germany). The intensity of GFP fluorescence expression was then quantitated from the in vivo images using a previously described method for calculating corrected total cell fluorescence (CTCF), where CTCF is equal to, Integrated Density−(Area of selected cell/fluorescence×Mean fluorescence of background readings) (Burgess et al., *Proc. Natl. Acad. Sci. USA* 107:12564 (2010); McCloy et al., *Cell cycle* (*Georgetown, Tex.*) 13:1400 (2014)).

Effect of scAAV8G9-optHLA-G on corneal vascularization in vivo: Neovascularization was monitored by slit-lamp biomicroscopy and photography, central corneal pachymetry (PachPen Handheld Pachymeter, Accutome, Malvern, Pa.), and intraocular pressure (IOP; Tonovet tonometer, Icare, Finland) were performed at day 0 (prior to wounding) and every 2-3 days for the following 56 days. Vascularization was quantified by converting each in vivo slit-lamp biomicroscopy image file to 8-bit via ImageJ and increasing the visualization of vasculature with the finding edges and contrast enhancement processes, along with inverting all black and white values. The converted images were then opened in GNU Image Manipulation Program (GIMP 2.8.20), a transparent overlay layer was added to each image file, vessels were manually traced on to the new layer, and finally, the area of traced vessels was converted to total pixel number using ImageJ.

Expression and re-establishment of immune tolerance by HLA-G in the injured cornea: Rabbits were euthanized and eyes were recovered and post fixed overnight, at 4° C., in neutral buffered formalin and then stored in 70% EtOH until being paraffin embedded. Tissue was sectioned at 5 µM and histopathologically evaluated for the quantitation of cornea vasculature (CD31) and the immune response using CD3, CD8, and CD4. Sections stained with hematoxylin and eosin were examined by light microscopy. The corneal histologic scoring scheme was modified from a previously described method (Mercadal et al., *J. Virol.* 67:3404 (1993)) and graded the following areas, degree of cellular infiltrate, extent of fibrosis, and extent of vascularization. Scores of 0-4 were assigned based on the following rubric: 0, no significant lesion; 1, low numbers of inflammatory cells, mild fibrosis, minimal vascularization; 2, moderate, diffuse stromal inflammatory cell infiltrates, fibrosis, or neovascularization; 3, moderate to marked diffuse stromal inflammatory cell infiltrate, fibrosis, or neovascularization; 4, marked, diffuse, cellular infiltrate, fibrosis, vascularization. Cumulative histologic scores were then analyzed and reported as mean±standard deviation (SD) per treatment group.

Immunohistochemistry: Cornea tissues were embedded in paraffin and using a microtome, 5 µm sections were cut and then mounted and dried onto slides. In order to stain the tissue sections and use Alexa Fluor conjugated secondary antibodies to image fluorescence, sections were deparaffinized and rehydrated. Deparaffinization was carried out by incubating slides twice, 5 minutes each, in xylenes. Using a decreasing ethanol gradient, tissue was rehydrated by sequentially moving the slides through two incubations in 100% ethanol for 3 minutes each, one incubation in 95%, one incubation in 80%, and finally rinsed in deionized water for at least five minutes. Before staining tissue sections, heat-induced epitope retrieval (HEIR) procedure was performed at 98° C. for 15-20 minutes to unmask epitopes of proteins that were crosslinked during the paraffinization process. Specifically, sections that were stained for HLA-G (Santa Cruz, sc-21799, dilution 1:50), GFP (Ayes, gfp-1020, dilution 1:500), CD3 (Biorbyt, orb323391, 1:100), CD4 (Invitrogen, MA1-81588, 1:100), and CD8 (Novus Biologicals, NB10064021, 1:100) were immersed into pre-heated citrate based antigen retrieval solution, pH 6.0 (Vector Laboratories, H-3300), while the CD31 (Abeam, ab199012, 1 µg/ml) epitope was retrieved in 1 mM EDTA, pH 8.0. After HEIR was completed, slides were allowed to cool for 20 minutes at room temperature and then sections were washed twice for 5 minutes each in TBS plus 0.025% Triton X-100 with gentle agitation. The non-specific binding sites within the tissues were then blocked by incubating the slides with 10% normal serum, tissues stained for HLA-G were blocked with normal horse serum while all others were blocked with normal goat serum, with 1% BSA in TBS for 1 hour at RT. Blocking solution was drained off of the slides and sections were then incubated overnight at 4° C. with primary antibody diluted appropriately in TBS with 1% BSA. After incubation, sections were washed two times, 5 minutes each, with TBS plus 0.025% Triton X-100 with gentle agitation to remove primary antibody that was non-specifically bound. A suitable fluorophore-conjugated secondary antibody was diluted according to manufacturer suggestions in TBS plus 1% BSA and was then added to each tissue section and incubated for 1 hour at room temperature with gentle agitation. Finally, slides were washed three times with TBS, five minutes each. Nuclei within each section were stained when coverslips were mounted with ProLong Diamond Antifade Mountant with DAPI (Molecular Probes, P36971). Images from each slide were taken using an Olympus IX83 research inverted microscope with a 40× objective (Olympus, Tokyo, Japan) and processed using Olympus cellSans life science imaging software.

AAV8G9 Biodistribution following Stromal Injection: Serum was collected prior to the start and at the completion of these experiments and analyzed for neutralizing antibodies generated to the AAV capsid. Additionally, the liver, brain, kidney, heart, and draining lymph nodes were harvested for vector biodistribution assays using Q-PCR.

Neutralizing Antibody Assay: The presence of neutralizing antibodies in rabbit serum was assayed using a previously described method with slight modifications (Li et al., *Gene Therapy* 19:288 (2012)). HEK293 cells were seeded in 24 well plates at $5 \times 10^4$ cells per well in 500 µl of complete DMEM (10% serum, 1% P/S). Cells were cultured for 24 hrs at 37° C. and 5% $CO_2$. Each rabbit's pre- and post-injection serum was serially diluted, starting with twofold and going up to 1:256, in DPBS to a final volume of 12.50. Serum dilutions were incubated with $3.84 \times 10^8$ viral genomes (7,680 genomes/cell) of AAV8G9-Luciferase for 2 hr at 4° C. The seeded HEK293 cells were then transduced with virus-serum mixtures for 48 hrs under optimal culture conditions before transduction efficiency was measured by a luciferase assay.

Luciferase Assay: Luciferase assays were conducted to measure the transduction efficiency of AAV8G9 in the presence of rabbit serum. Promega Luciferase Assay System was performed as follows. A 1× lysis reagent was prepared by diluting 5× Promega Passive Lysis Buffer in ddH$_2$O. Media was aspirated and cells lysed by adding 250 µl of lysis reagent to each well of HEK293 cells and shaking the plate at room temp for 20 minutes. A mixture of 100 µl of lysed cells and 100 µl of Luciferase Assay Reagent was added to each well of a 96-well plate and using the Perkin Elmer Victor³ multilabel plate reader luminescence was measured as counts/second (CPS). Protein concentration was measured using a Nanodrop 2000c spectrophotometer and for each sample luciferase activity was normalized to the total protein concentration and reported as CPS/[P].

Results

Figure 1B:
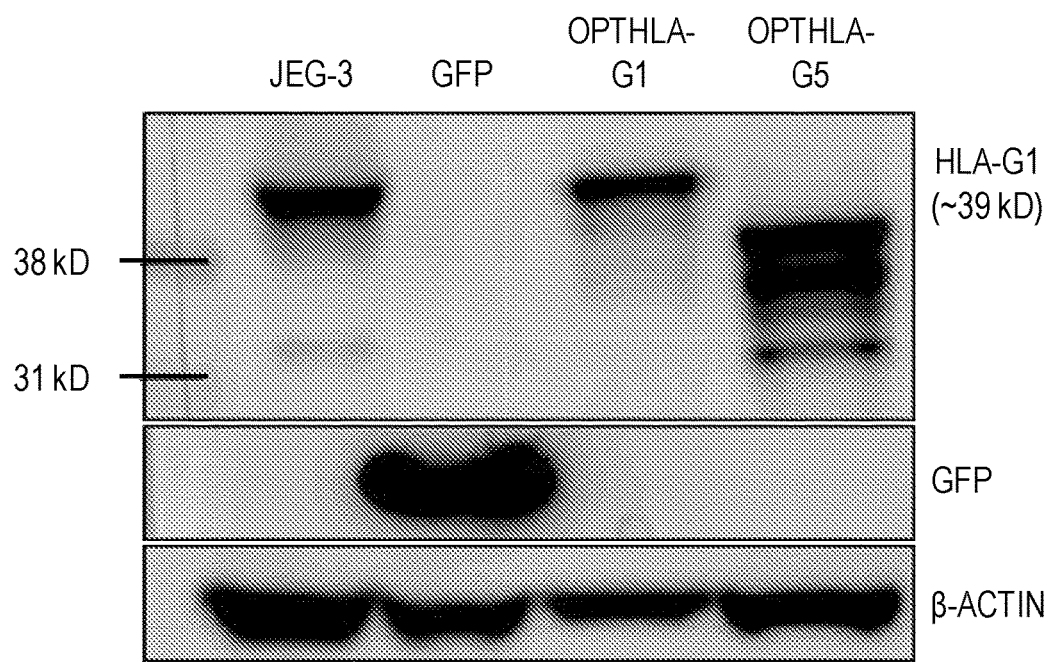
Figure 1C:
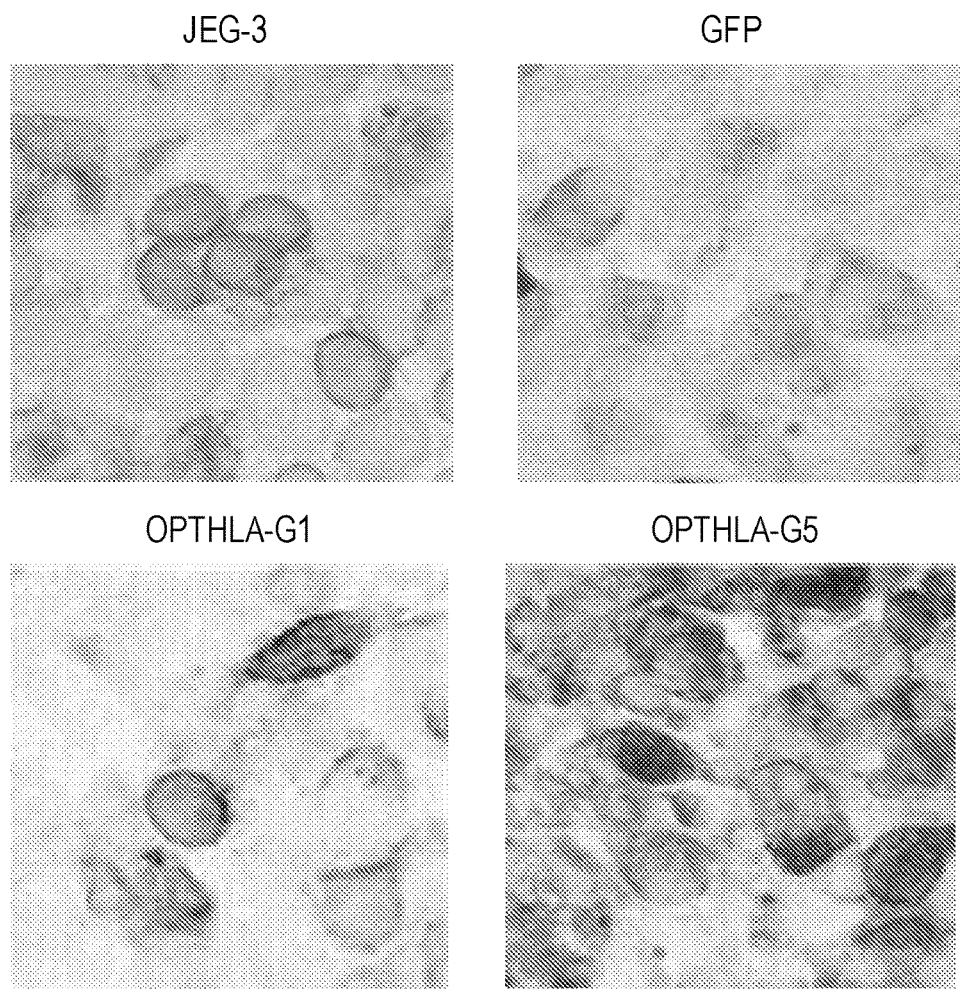
Figure 2A:
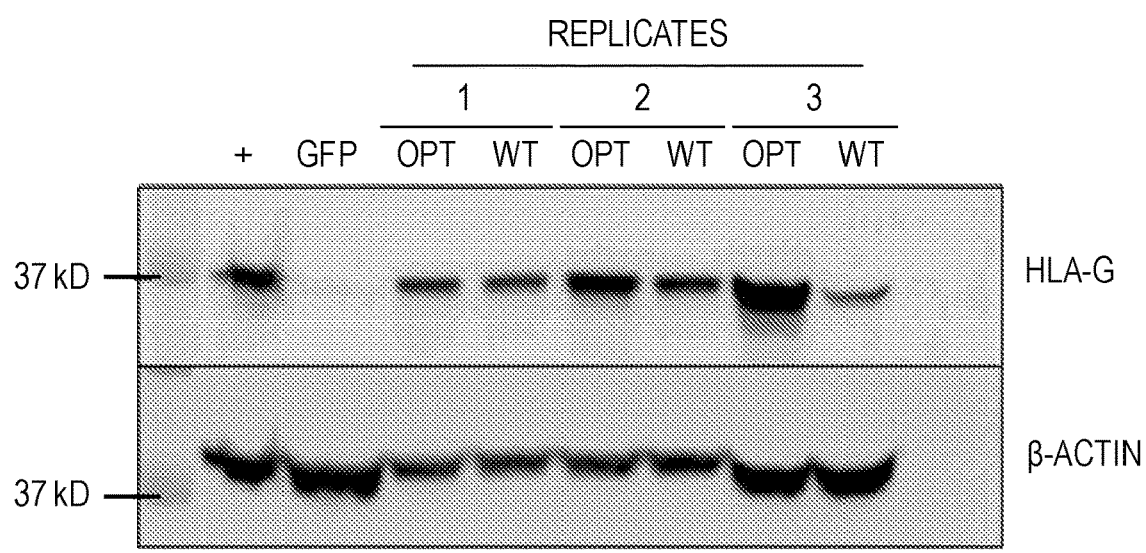
FIGS. 2A-2B show a comparison of HLA-G abundance from WT or codon optimized cDNA. A) Identical plasmid contexts containing the WT HLA-G cDNA or codon optimized HLA-G cDNA were used in separate 293 cell transfections. Lysate was recovered 3 days post-transfection and analyzed for the indicated proteins by Western blot. B) Quantitation based on Western blot densitometry of the data depicted in A. Opt=codon optimized, ORF=open reading frame.
Figure 2B:
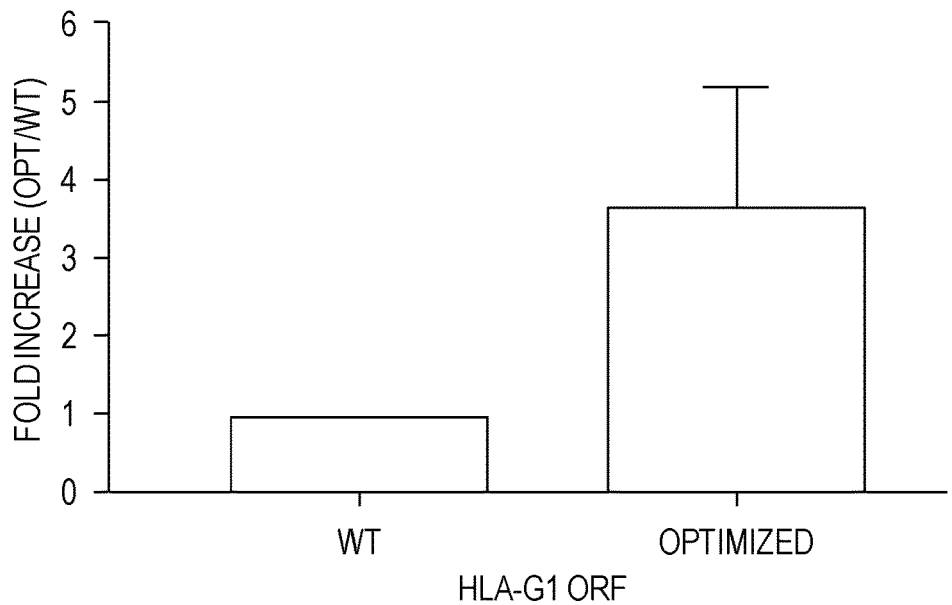

Optimized AAV HLA-G construct and in vitro expression: Initially the HLA-G1 cDNA (accession BC021708) was codon optimized for theoretically enhanced transgene production in human cells, as well as to remove unwanted alternative open reading frames (ORFs) (FIG. 1A) (Li et al., Proc. Natl. Acad. Sci. USA 106:10770 (2009)). Western blot detection of plasmid-borne HLA-G1 from either WT or codon optimized HLA-G1 cDNA demonstrated a consistent 3-fold elevation when using the codon optimized version (optHLA-G1) in human embryonic 293 cells (FIGS. 2A-2B). Next, the optHLA-G1 transmembrane domain was deleted to generate optHLA-G5 cDNA, and both optHLA-G1 and optHLA-G5 were cloned into a self-complementary AAV plasmid context (FIG. 1A). Western blot analysis following transfections of these plasmids in 293 cells generated an anticipated single band at 39 kDA for optHLA-G1 and the expected smaller product for optHLA-G5, which accompanied by smaller forms, one of which appeared to match the size of the smaller HLA-G form observed in the JEG-3 placenta control cells at about 32 kDA (FIG. 1B). Next, the intracellular localization of HLA-G1 (transmembrane) and HLA-G5 (soluble and secreted) were investigated via immunocytochemistry following transfections in 293 cells. Immunostaining of JEG-3 cells demonstrated cytoplasmic, surface, and extracellular staining. In contrast, 293 cells transfected with optHLA-G1 demonstrated primarily surface membrane staining while optHLA-G5 transfected cells appear to have more staining in the cytosol and extracellular matrix (FIG. 10). These collective results demonstrate that the optimized HLA-G isoforms result in efficient protein production and expected HLA-G localization.

Figure 3:
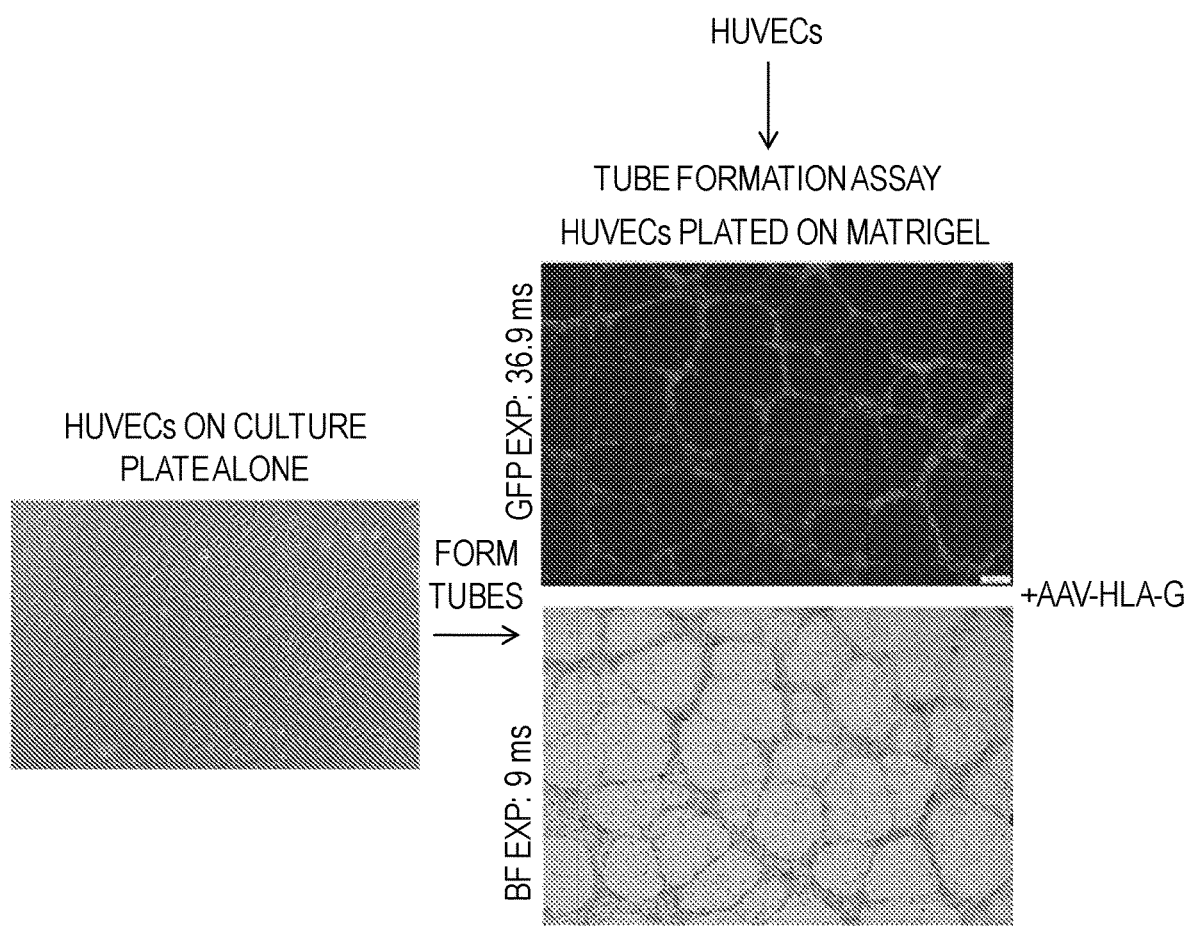
FIG. 3 shows that AAV-HLA-G has an anti-angiogenesis function in human cells.
Figure 4:
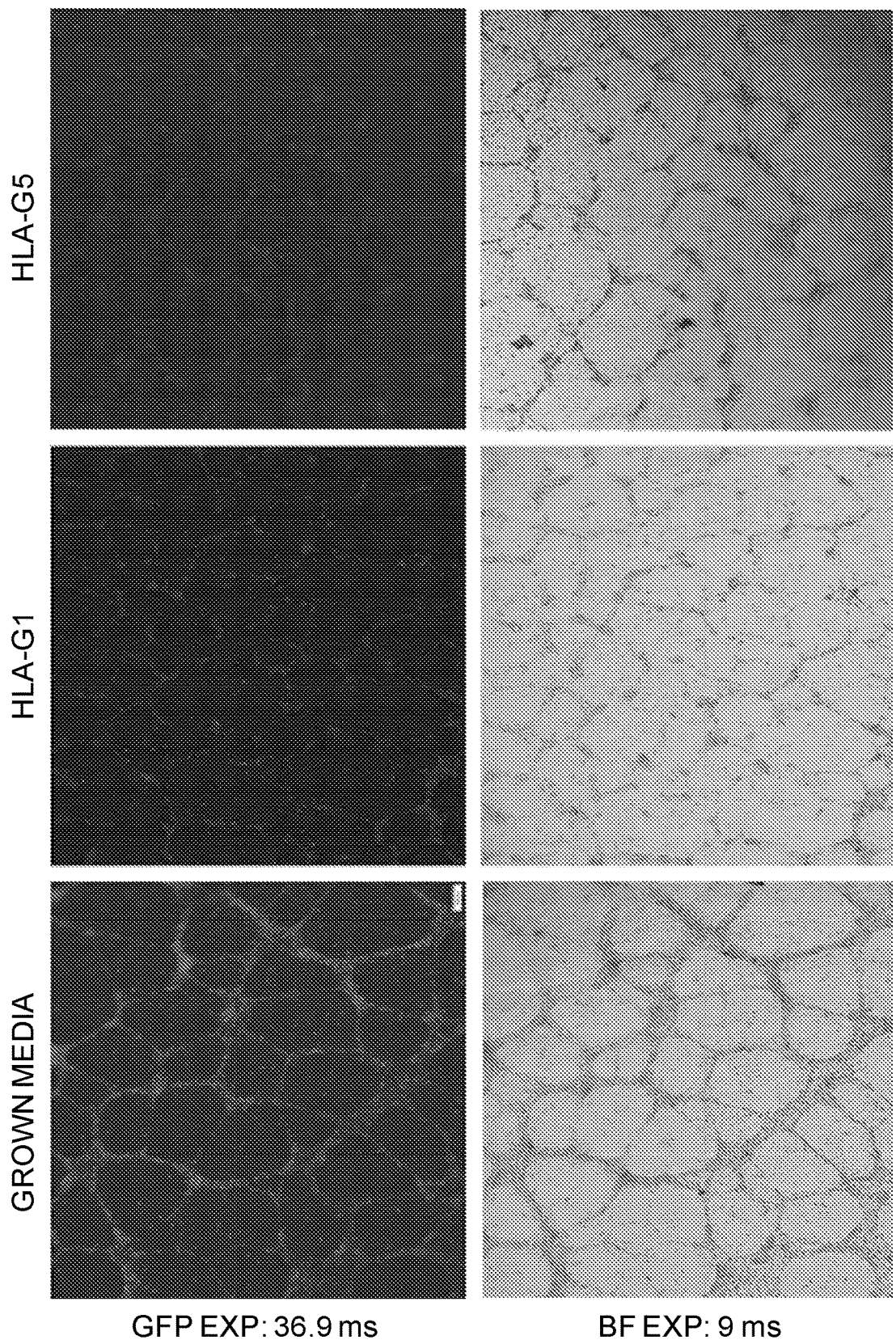
FIG. 4 shows the effect of HLA-G1 and HLA-G5 expression in an endothelial tube assay as a model of anti-angiogenesis.

Anti-angiogenesis Function of HLA-G: A tube formation assay in human umbilical vascular endothelial cells (HUVEC) was performed to analyze the anti-angiogenic activity of HLA-G. HUVEC were cultured on Matrigel and spontaneously formed tubes (FIG. 3). The cells were then infected with the HLA-G1 or HLA-G5 vectors 1×10⁴ viral genomes/cell and culture for 24 hours. FIG. 4 shows that both vectors decreased tube formation substantially, indicating the ability of both HLA-G1 and HLA-G5 to inhibit angiogenesis.

Figure 5A:
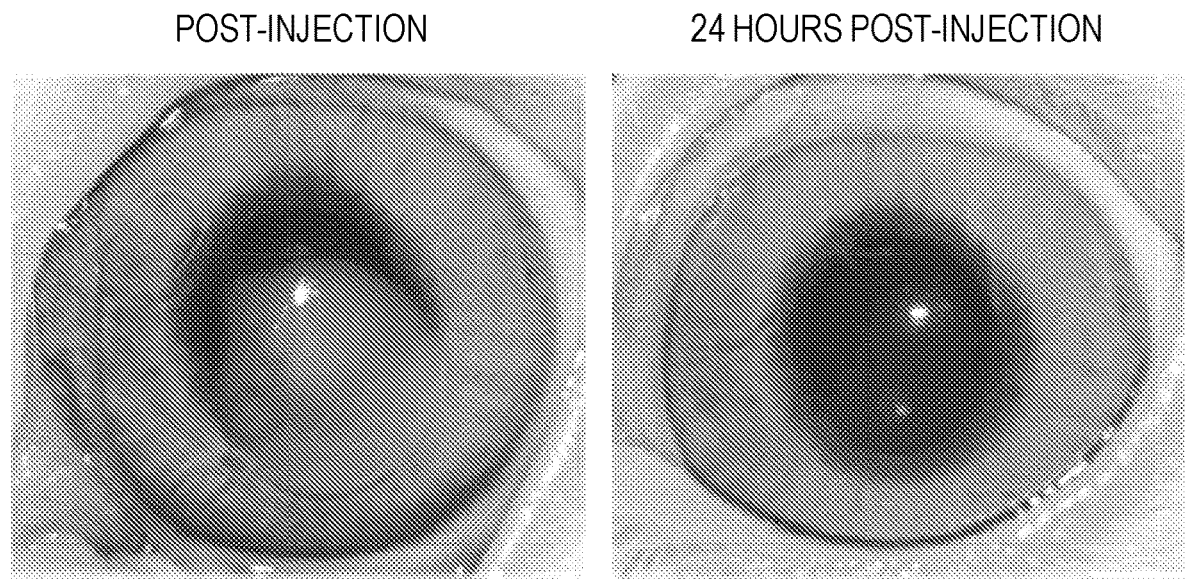
FIGS. 5A-5C show scAAV8G9 mediates gene delivery in the rabbit cornea. A) Vector injection of 50 µl into the rabbit corneal stroma causes transient corneal cloudiness. B) Quantitation of the area of cornea covered by the injection. C) Representative in vivo images depicting intensity of GFP expression and quantitation of GFP intensity of the indicted injectable at the indicated time point. (P<0.0009). P.I.=post-injection, sc=self-complementary.
Figure 5B:
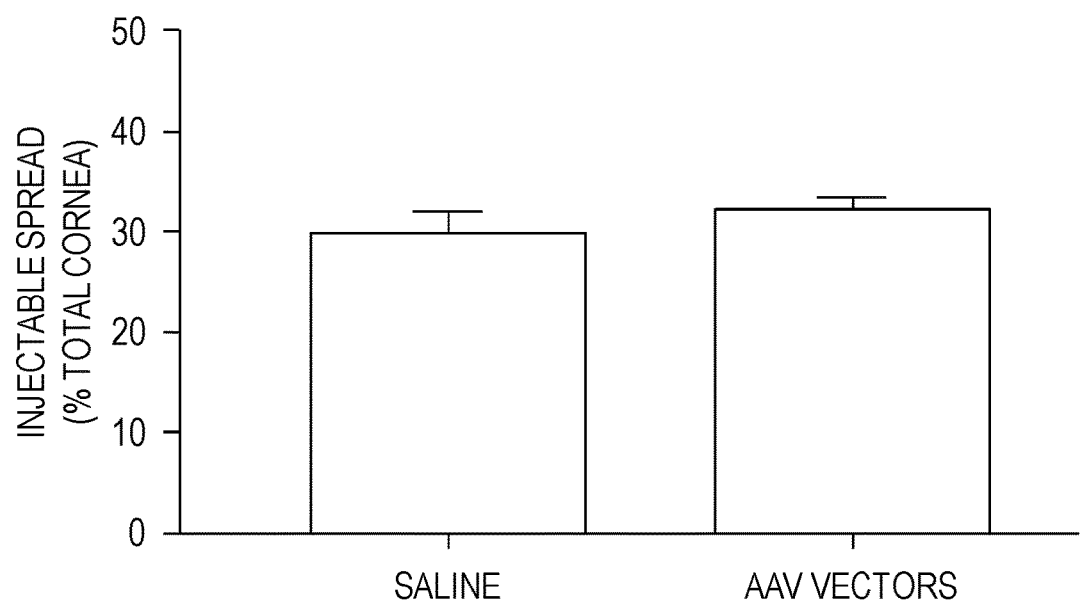
Figure 5C:
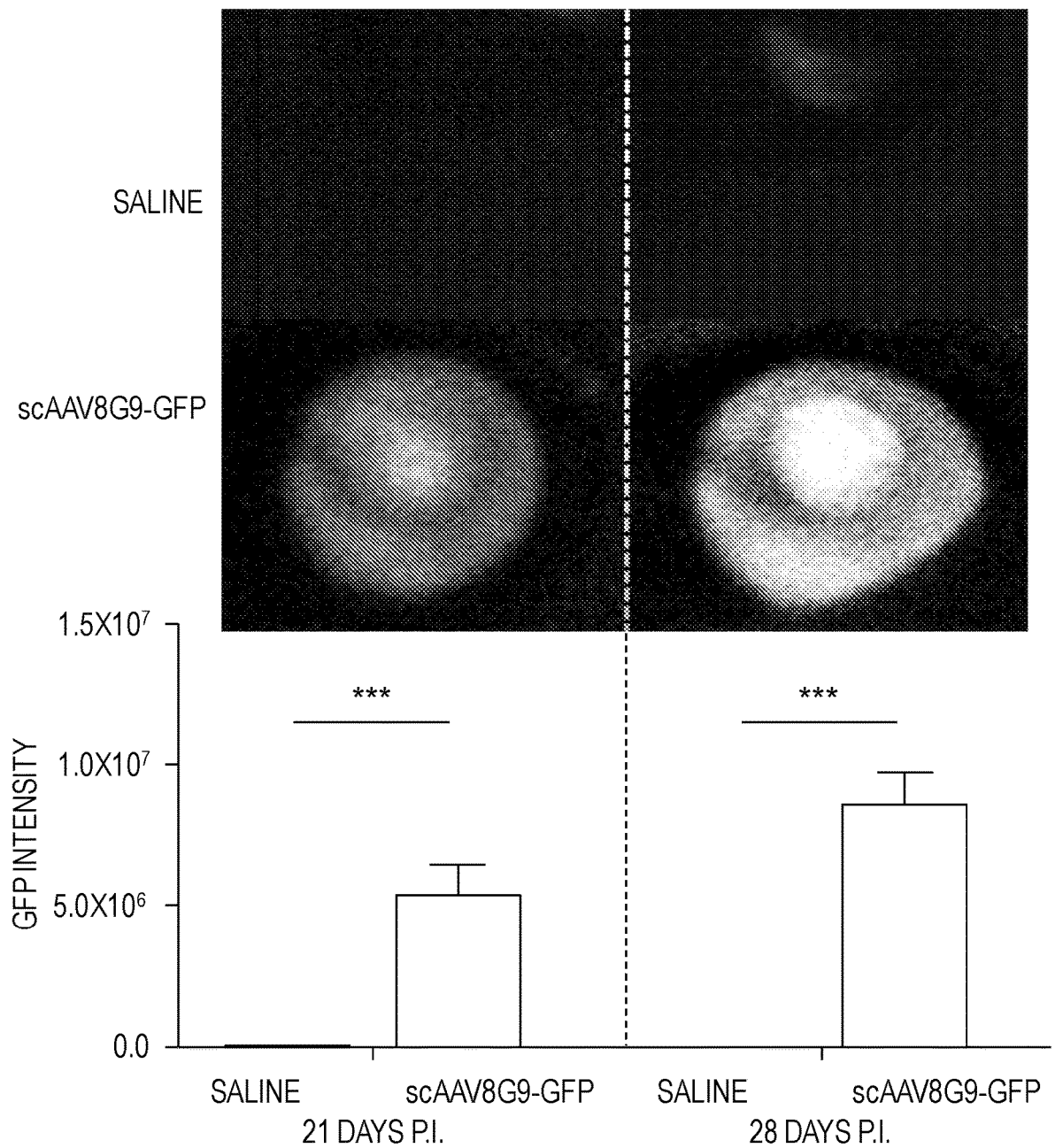

AAV8G9 capsid mediates efficient gene delivery to the rabbit cornea: The chimeric capsid "8G9", which is the AAV8 capsid sequence engrafted with the putative AAV9 galactose receptor binding domain, was found superior for human cornea transduction following intrastromal injection (Vance et al., Scientific Rep. 6:22131 (2016)). To determine if AAV8G9 also transduces the rabbit cornea, a self-complementary (sc) JET-GFP reporter cassette was packaged in the AAV8G9 capsid and administered to the rabbit cornea via a 50 µl intrastromal injection of 5×10¹⁰ viral genomes (vg) (McCarty et al., Gene Therapy 8:1248 (2001)). Following intrastromal injection of balanced salt solution (BSS) or scAAV8G9-GFP, an immediate central corneal opacity throughout approximately 30% of the central cornea developed (FIGS. 5A and 5B). This opacity completely resolved within 24 hours of the injection (FIG. 5A). Using live imaging, GFP fluorescence was detected in the central cornea, at the location of vector injection, twenty-one days post-injection (FIG. 5C). Quantitation of the signal demonstrated peak GFP intensity at 28 days post-injection (FIG. 5C).

Figure 6A:
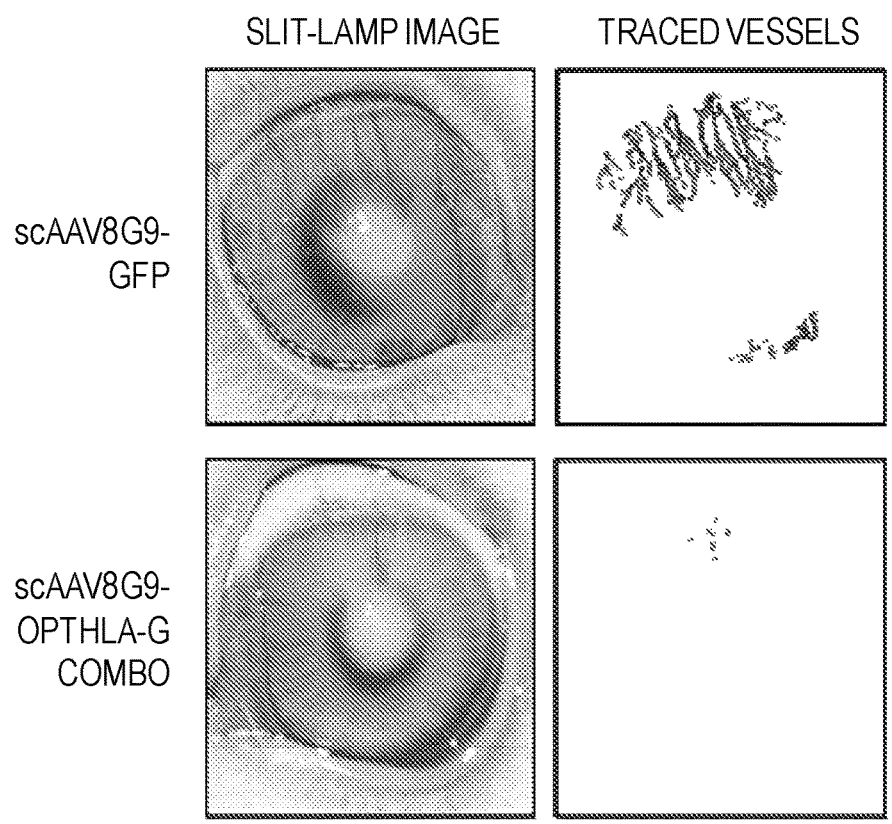
FIGS. 6A-6B show scAAV8G9-optHLA-G Combo prevents burn-induced cornea vascularization. Rabbit corneas were centrally burned seven days prior to a cornea intrastromal injection of scAAV8G9-GFP or scAAV8G9-optHLA-G Combo (isoforms 1 and 5 at a 1:1 ratio). A) Representative in vivo images depicting vascularization alongside images of vascularization tracings of treated corneas 42 days post-injection with the indicated vectors. B) Quantitation of the traced area of vascularization immediately after corneal burn (day 0), 3 days after injection with the indicated vectors (day 10), and the last experimental time point (day 56) ($P<0.001$ at day 10 and $P<0.002$ at day 56). sc=self-complementary.
Figure 6B:
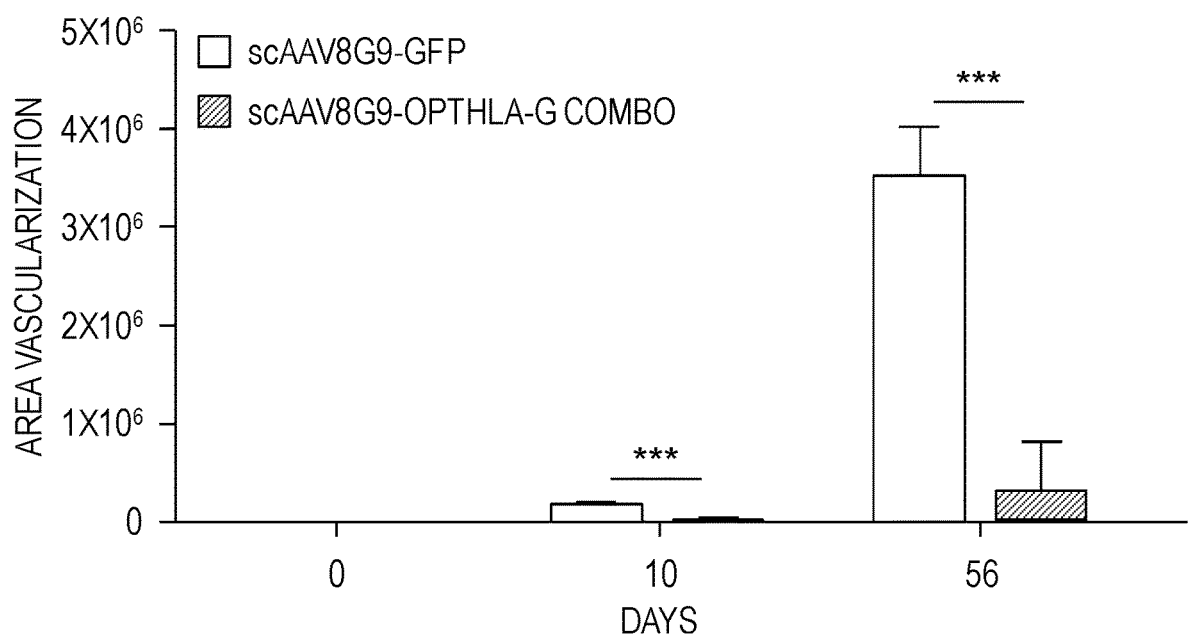
Figure 7A:
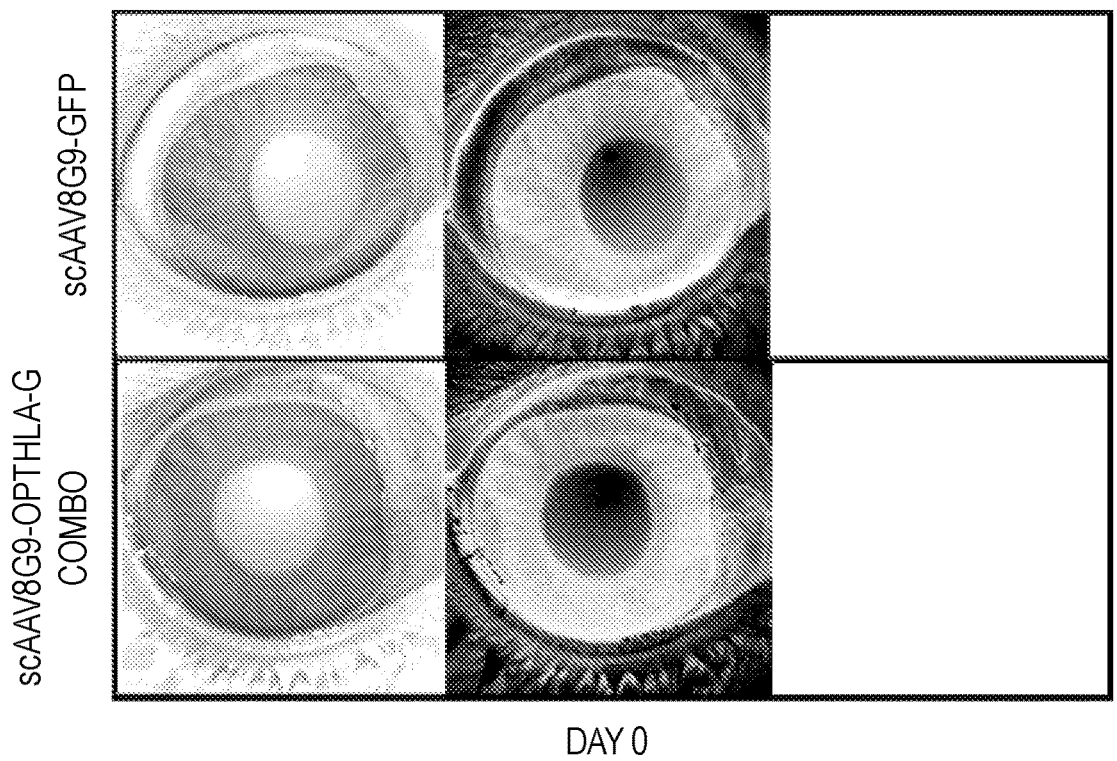
FIGS. 7A-7C show burn-induced cornea vascularization analysis and quantitation of in vivo images. Centrally burned rabbit corneas were given an intrastromal injection of either scAAV8G9-GFP or scAAV8G9-optHLA-G Combo seven days after injury was induced. A-C) Representative images depicting traced vascularization from in vivo live images of treated corneas with the indicated vectors at the indicated time points to quantitate the total area of vessel ingrowth. sc=self-complementary.
Figure 7B:
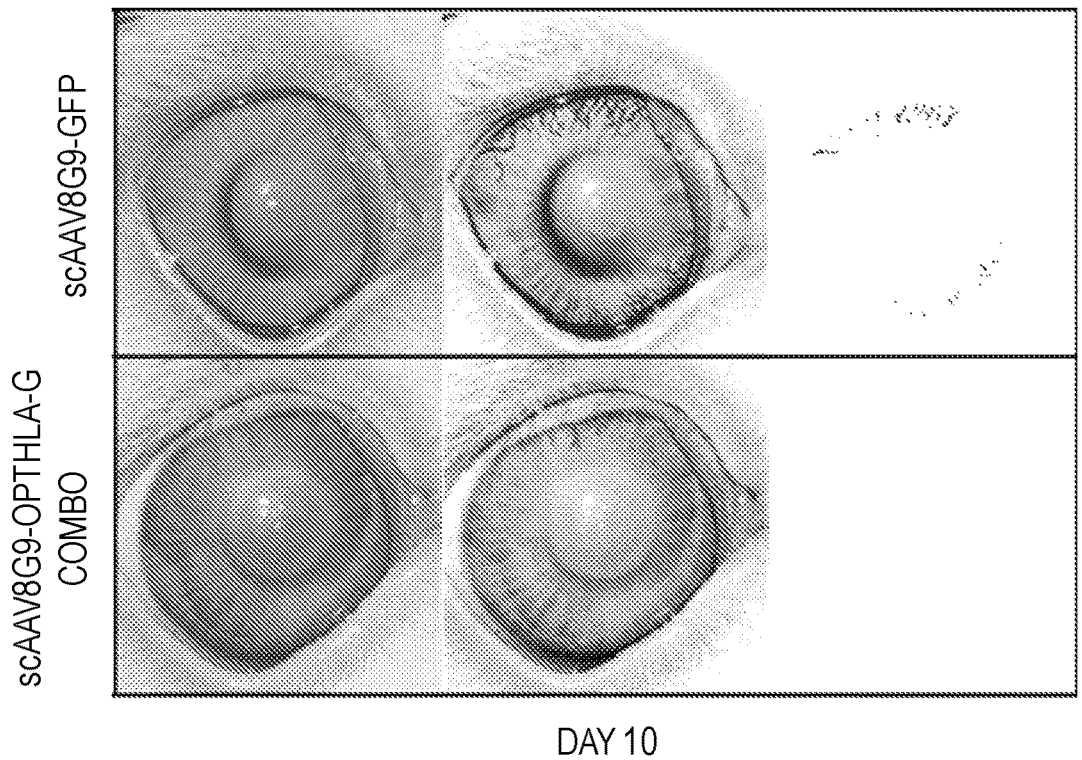
Figure 7C:
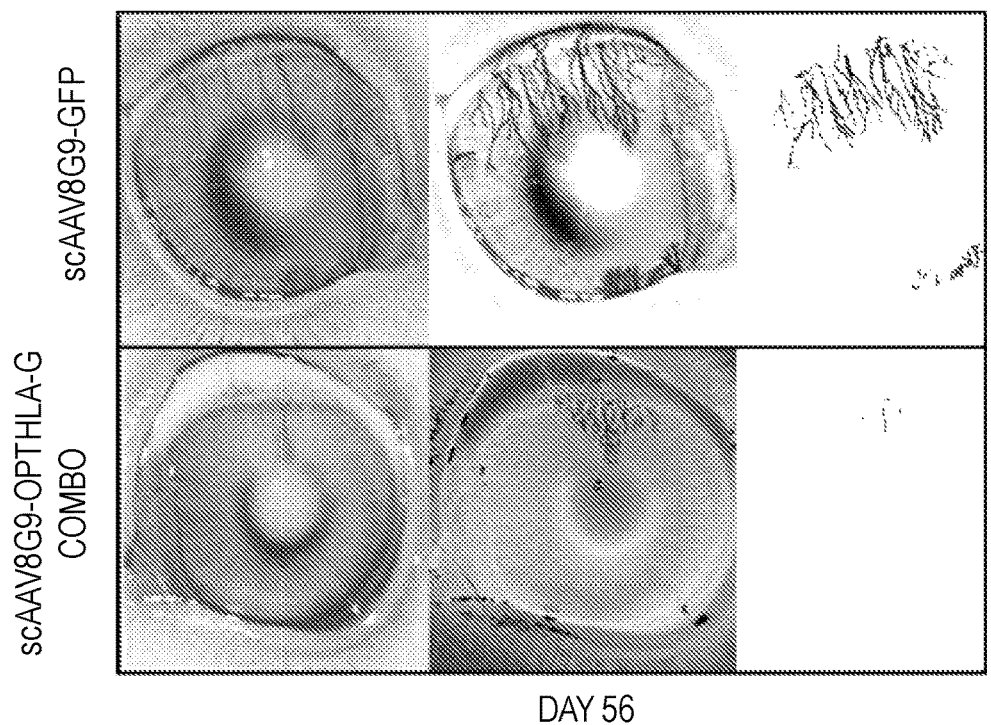
Figure 8A:
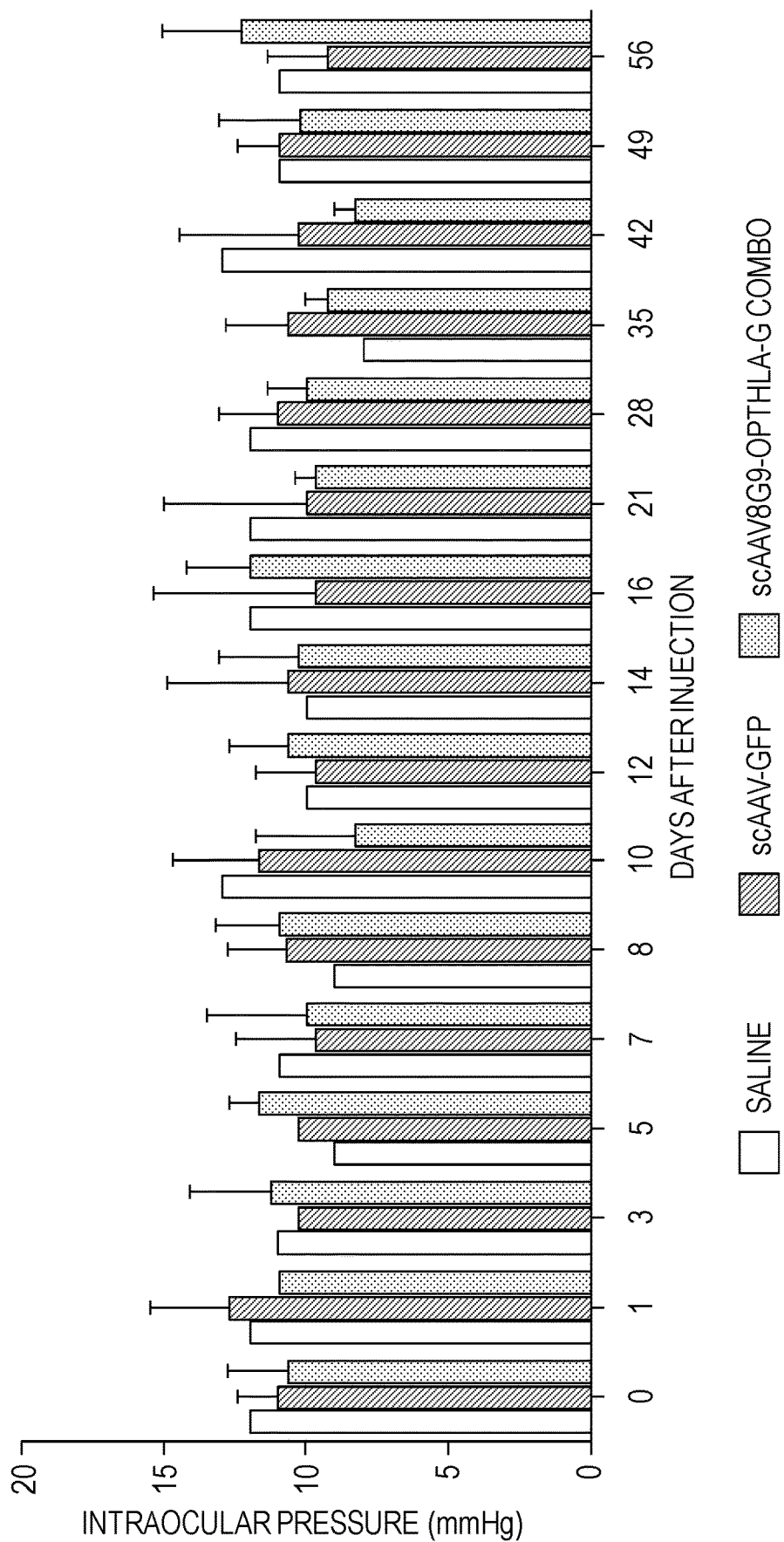
FIGS. 8A-8B show intraocular pressure following AAV vector cornea injections. Rabbit corneas were burned centrally eight days prior to a cornea intrastromal injection of saline, scAAV8G9-GFP, or scAAV8G9-optHLA-G Combo (isoforms 1 and 5 at a 1:1 ratio). A) Intraocular pressure is reported on the indicated day post-injection. B) Central corneal thickness is reported on the indicated day post-injection.
Figure 8B:
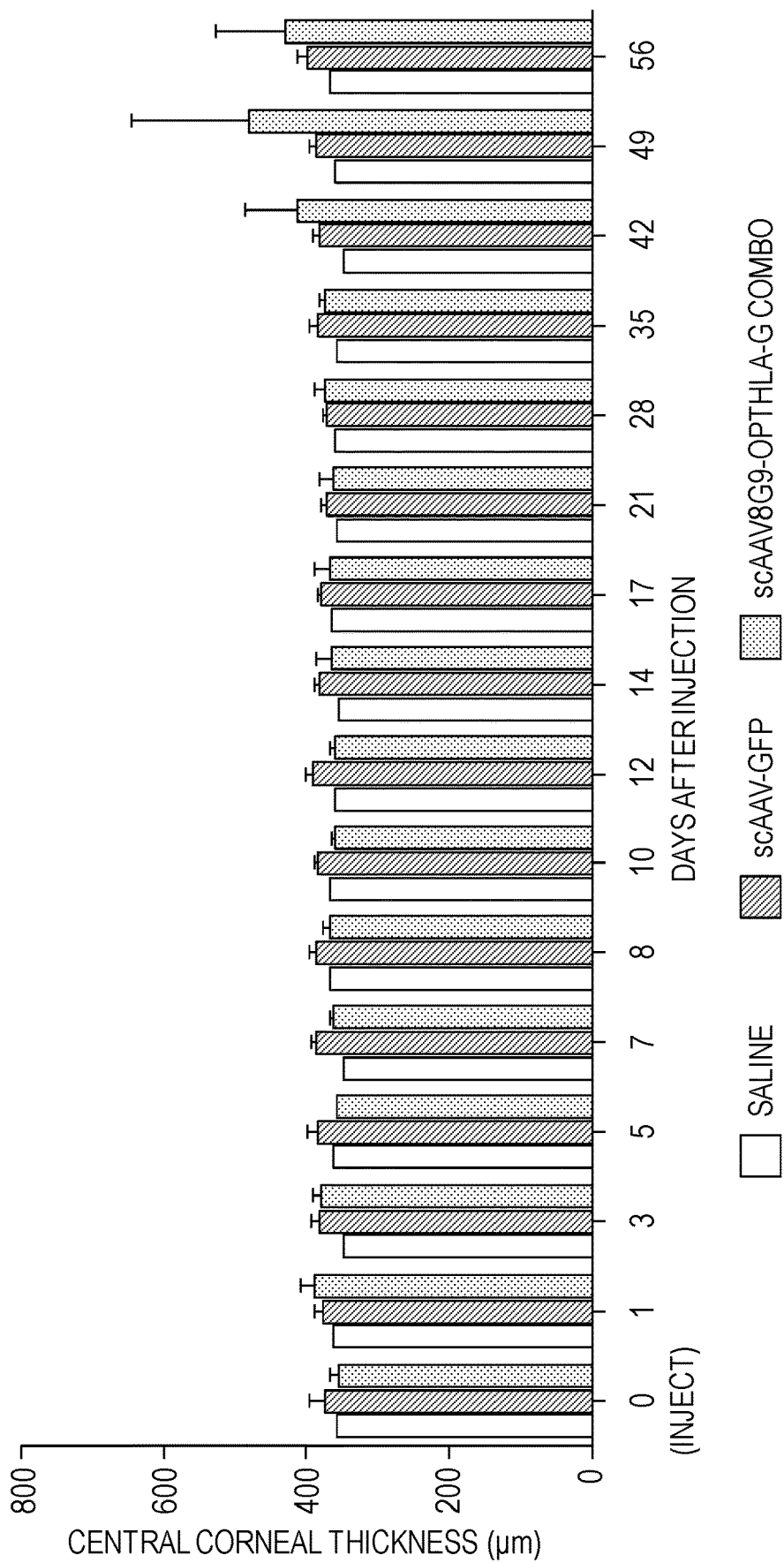

Effect of scAAV8G9-optHLA-G on corneal vascularization in vivo: Although HLA-G homologs have not been identified in nonprimate species, a previous report using HLA-G protein demonstrated HLA-G's function, consistent with its known roles in humans, in a rabbit model (Fons et al., Blood 108:2608 (2006)). Additionally, the rabbit eye is similar in structure and size to the human eye and is perhaps the most popular model for ocular research. Given that the AAV8G9 was validated for rabbit cornea transduction (FIGS. 5A-5C), the optHLA-G plasmid constructs were used to produce preclinical scAAV8G9 vectors. To mimic a clinically relevant scenario, rabbits were anesthetized and corneas were injured prior to AAV vector injections via a central 5 mm corneal chemical NaOH burn. Seven days after burn injury, intrastromal injections with scAAV8G9 vectors encoding GFP or, due to the exact roles of HLA-G isoforms being unknown and in an effort to increase the chances of seeing a therapeutic effect, optHLA-G1+optHLA-G5 at a 1:1 ratio (optHLA-G Combo). Corneal vascularization began to advance past the limbus and into the cornea tissue approximately 7 days after injury, with there being a significant difference between treatment groups by day 10 post-injury ($p<0.001$) (FIG. 6A). It should be noted that the actual burn leaves a central corneal opacity that does not resolve over the experimental period. Quantitation of the area of vascularization using ImageJ demonstrated increased vessel ingrowth at every experimental time point, with maximal vascularization in corneas treated with scAAV8G9-GFP, at 56 days post-injury. In contrast, 2 months post-injury, subjects that received scAAV8G9-optHLA-G Combo did not manifest any significant vessel formation, which is 10-fold less than the scAAV8G9-GFP treated eyes ($P<0,002$) (FIGS. 6A and 6B and 7A-7C). There were no significant changes associated with intraocular pressure or corneal thickness by 24 hours after injection and throughout the experimental evaluation period (FIGS. 8A-8B).

Figure 9A:
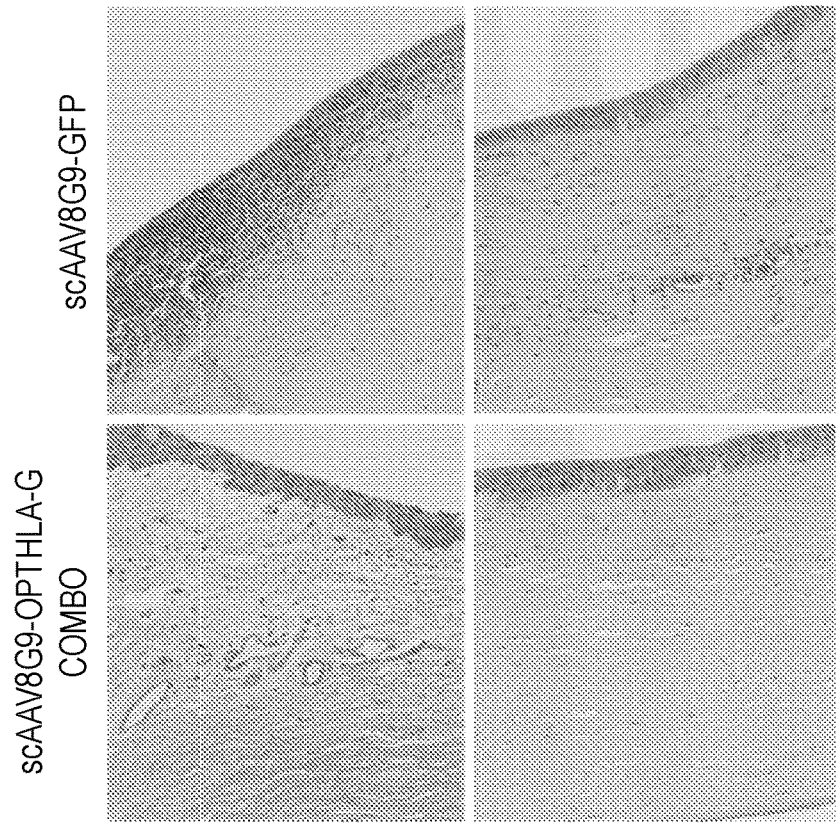
FIGS. 9A-9B show scAAV8G9-optHLA-G Combo prevents cornea burn-induced vascularization and immune cell infiltration. Rabbit cornea sections were acquired 60 days following the injection of indicated vectors into trauma induced corneas and stained with hematoxylin and eosin. A) Representative images of processed sections treated with the indicated vector preparation. B) Quantification of clinical histological exam scores of all H&E sections presented in (A) ($P<0.0005$).
Figure 9B:
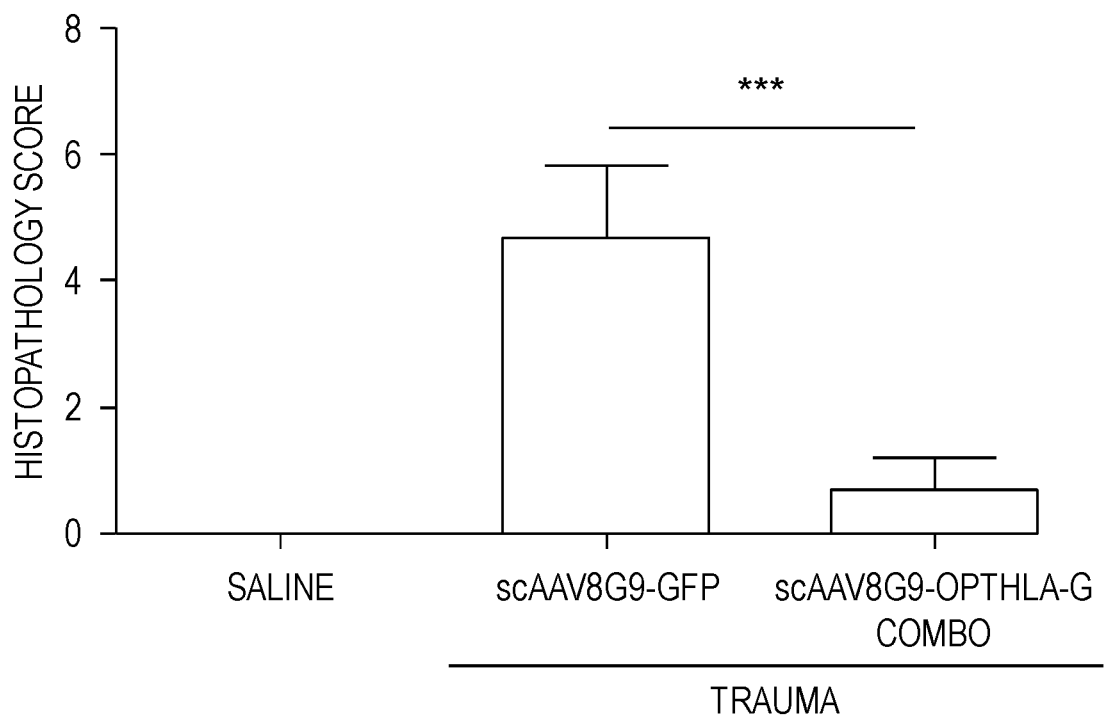

Expression and re-establishment of immune tolerance by HLA-G in the injured cornea: Following 8 weeks of observation, tissues were recovered for histological analysis. Histology of injury induced corneas injected with scAAV8G9-GFP revealed histologic changes consisting of central corneal mononuclear cellular infiltrate, vascularization into the central cornea, and mild to moderate amount of fibrosis (FIG. 9A). While in comparison, histological analysis of injured corneas that were injected with scAAV8G9-optHLA-G Combo, had minimal cellular infiltrates and no vascularization and as a result were significantly different from corneas injected with the GFP control vector (FIG. 9B). In fact, the mean cumulative histology scores of post-injury corneas injected with scAAV8G9-HLA-G Combo was significantly lower than mean scores for corneas injected with the GFP control vector ($P<0.0005$) (FIG. 9B).

Figure 10A:
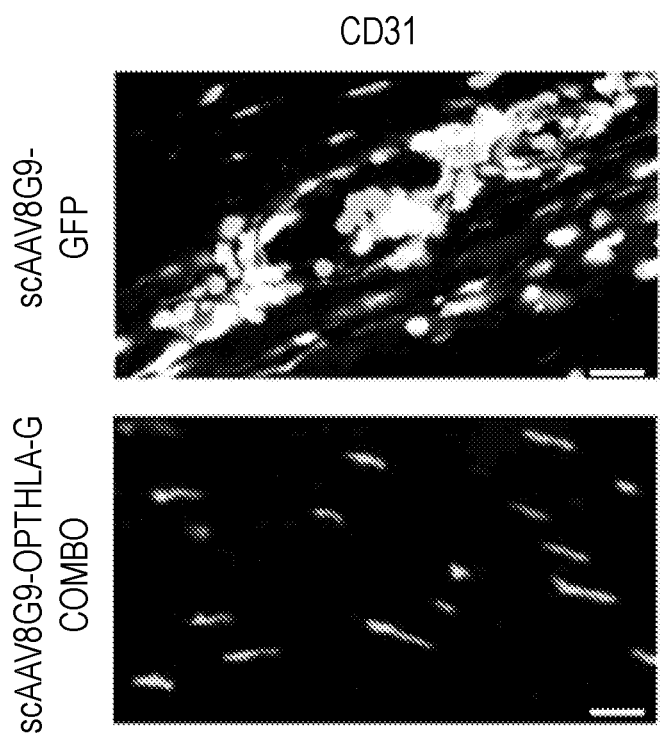
FIGS. 10A-10C show scAAV8G9-optHLA-G Combo prevents cornea burn-induced vascularization and cytotoxic T-cell infiltration. Rabbit cornea sections were acquired 60 days following the injection of indicated vectors into burn corneas and stained for an endothelial cell marker (CD31), T cell markers, and for transgene abundance in the indicated treatment groups. Scale bars=(A) 10 µm, (B) 5 µm, (C) 20 µm.
Figure 10B:
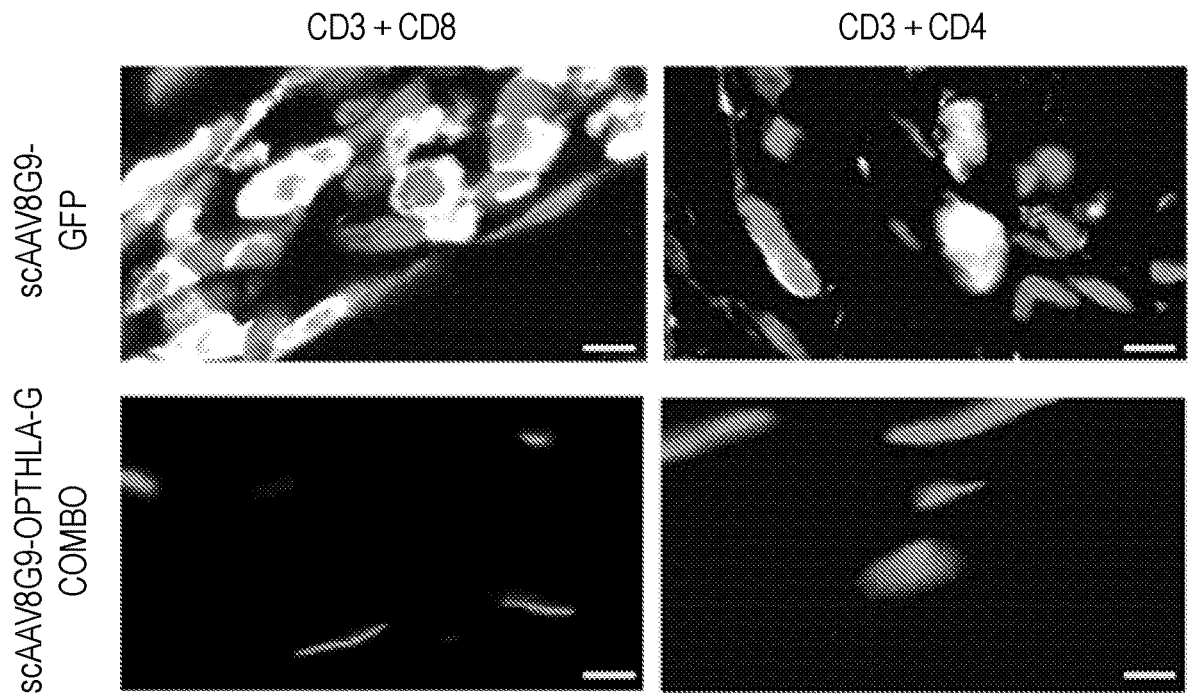

In addition to H&E staining, immunofluorescence was used to confirm blood vessels in the central cornea by revealing the presence of endothelial intercellular junction cell marker, CD31 (FIG. 10A). CD3 immunostaining confirmed that the majority of infiltrating cells in the scAAV8G9-GFP injured corneas were positive for the CD3 surface antigen (FIG. 10B). A subset of this population also stained positive for CD8, demonstrating the influx of cytotoxic T cells following cornea injury (FIG. 10B). A smaller subset of this T cell population proved to be CD4⁺, also demonstrating the presence of helper T cells.

Figure 10C:
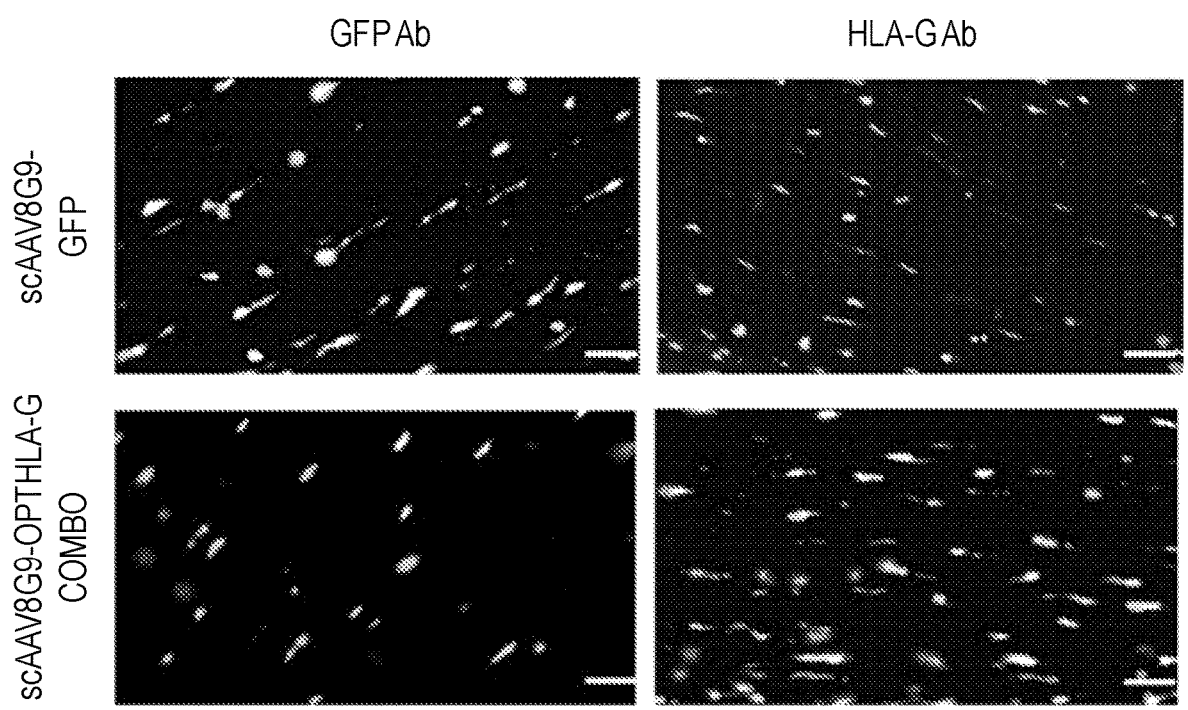
Figure 11A:
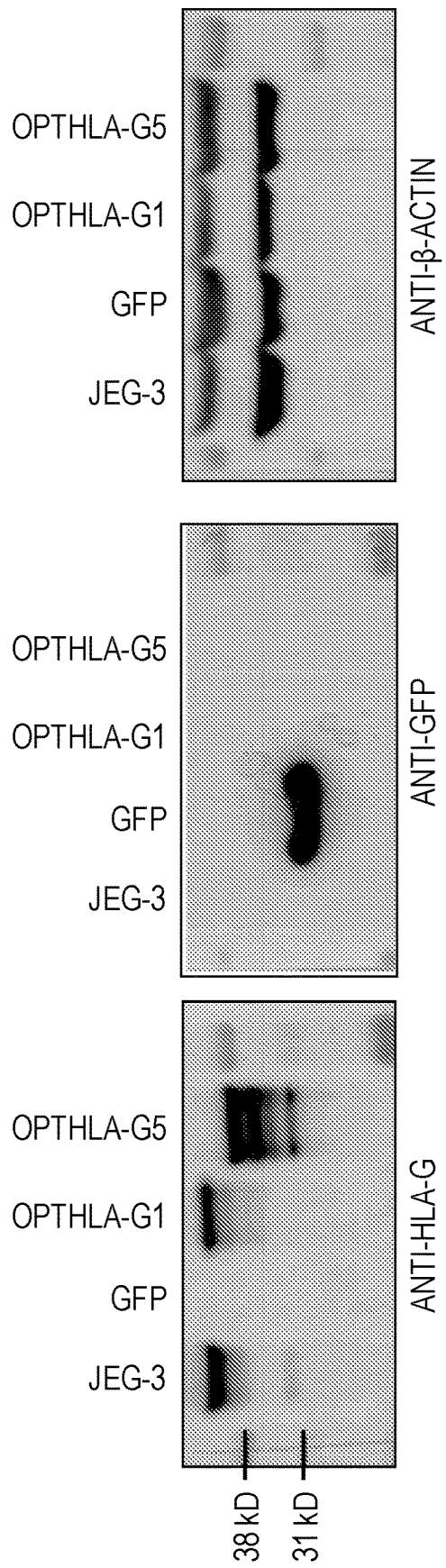
FIGS. 11A-11B show western blot analysis. Full-length Western blot images for (A) HLA-G, GFP and beta-actin for confirmation of optHLA-G isoform production in 293 cells and (B) HLA-G and beta-actin expression in lysate recovered 3 days post transfection of identical plasmid contexts containing the WT HLA-G cDNA or codon optimized HLA-G cDNA. The predicted target sizes for HLA-G, GFP and beta-actin are 39 kDa, 27 kDa. and 42 kDa, respectively.
Figure 11B:
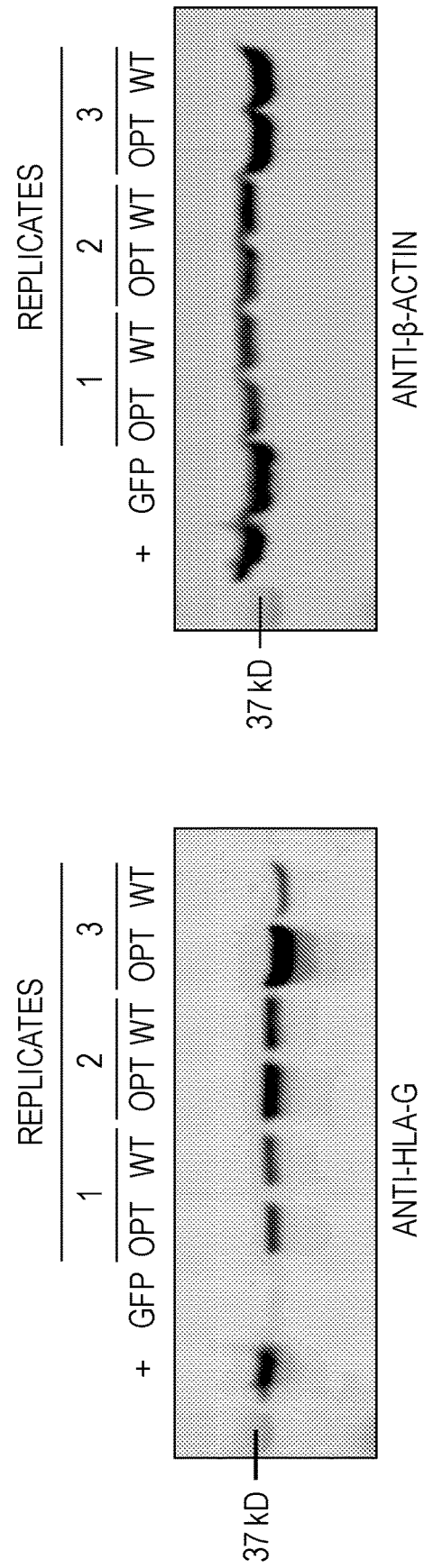

Cornea tissue was also analyzed to confirm vector derived transgene production using immunofluorescence. Similar to our reported human results (Vance et al., Scientific Rep. 6:22131 (2016)), GFP was found present throughout the cornea of rabbits given scAAV8G9-GFP. As expected, HLA-G proteins were evident only in corneas injected with scAAV8G9-optHLA-G Combo, thereby correlating the therapeutic effect to HLA-G (FIG. 10C).

AAV8G9 Biodistribution following Corneal Intrastromal Injection: It is of importance for potential clinical applications to determine the biodistribution of persistent AAV vectors following scAAV8G9 intrastromal injections, being this route of administration has not been done yet in the clinic. To do this, total DNA was recovered from samples of liver and two brain regions; the trigeminal nerve nuclei, that innervates the cornea, and the lateral *geniculate* nucleus that innervates the retina.

PCR using primers to the transgenic cassette failed to detect any viral genomes outside of the cornea, in tested tissues, independent of the conclusion of these experiments. Despite this, at the conclusion of the study, a strong scAAV8G9 capsid-specific neutralizing antibody response was detected in one of the rabbits that received scAAV8G9-GFP treatment and had developed extensive corneal vascularization, with a titer of 1/256 (Table 1). Two other rabbits demonstrated a very mild antibody response to the scAAV8G9 capsid, independent of the transgene or the emergence of vascularization (Table 1).

TABLE 1

| Animal ID | Serum Dilution |
|---|---|
| Saline | |
| Rabbit 1 | No Ab |
| scAAV8G9-GFP | |
| Rabbit 6 | 1:2 |
| Rabbit 7 | No Ab |
| Rabbit 8 | 1:256 |
| scAAV8G9-optHLA-G Combo | |
| Rabbit 12 | 1:4 |
| Rabbit 13 | No Ab |
| Rabbit 14 | No Ab |

DISCUSSION

Corneal vascularization, which affects over 1.4 million people per year in the United States alone, is elicited by one of two kinds of conditions, inflammation or hypoxia. Inflammation and/or hypoxia can be the result of a variety of insults including, bacterial or viral infection, autoimmune or degenerative diseases, physical trauma/manipulation, extended wear of contact lenses, chemical burns or toxic contamination. The invasion of vessels originating in the limbus not only affects visual acuity or occludes vision but also disrupts corneal immune homeostasis resulting in secondary conditions, such as increased inflammation and scarring, and is a major component in developing dry eye and corneal transplant rejection. Current drug modalities to treat vascularization rely on frequent administration and are only partially effective with serious vision threatening side-effects. More invasive procedures such as argon laser photocoagulation and transection are not particularly successful depending on the diagnosis and are increasingly less employed. Therefore, a single dose therapeutic capable of preventing, or inducing regression of vasculature, without vision threatening side-effects is needed to replace the current corneal vascularization treatment deficit. Towards this end, AAV gene delivery of codon optimized HLA-G isoforms was employed post-insult in rabbit corneas. Although incompletely understood, the effects of HLA-G are multi-factorial and perhaps natural in the eye, as HLA-G has been hypothesized to play a role in ocular immune privilege (Carosella et al., *Adv. Immunol.* 127:33 (2015)). Furthermore, its inherent function in fetal maternal immune tolerance implies that in humans, HLA-G is a "self" protein, an attribute important for successful gene therapy approaches. Following in vitro characterization and vector validation of scAAV8G9-optHLA-G, the experimental data demonstrate, with remarkable significance, two important therapeutic outcomes: i) near complete inhibition of corneal vascularization when administered post-trauma (FIGS. 6A-6B), and ii) maintenance of immune homeostasis by prevention of immune cell infiltration of the cornea (FIGS. 9A-9B). Further characterization for anticipated clinical applications indicated that AAV vectors injected into the burned cornea were able to elicit a systemic antibody response to the viral capsid (Table 1). However, in tissues that were tested, two months post-injection, no transgenic genomes were detected outside of the cornea.

Initially, the codon usage of HLA-G1 was altered for envisioned human applications in a manner that increased overall abundance, compared to WT HLA-G cDNA, and to eliminate alternative ORFs which can elicit CTLs following systemic gene therapy (FIGS. 2A-2B) (Li et al., *Proc. Natl. Acad. Sci. USA* 106:10770 (2009))[19]. Although codon optimization is inconsistently successful (Hirsch et al., *Mol. Therapy* 21:2205 (2013); Wang et al., *Proc. Natl. Acad. Sci, USA* 97:13714 (2000)), in the case of HLA-G1 the results demonstrate 3-fold increased abundance using the synthetic ORF, which could be due, in part, to altered post-transcriptional regulation by microRNAs targeting WT HLA-G (Sethupathy et al., *Trends Genetics* 24:489 (2008); Vasudevan et al., *Science* 318:1931 (2007)). Conceptually, this allows a concomitant dose decrease and, based on the available AAV vector results in humans, lower administered doses result in less vector related immune complications and better therapeutic outcomes (Salganik et al., *Microbiol. Spectr.* 3:doi:10.1128/microbiolspec.MDNA3-0052-2014 (2015)). To our knowledge, this is the first reported immune response to AAV gene therapy in the cornea, which is likely elicited by the foreign epitopes associated with the AAV vector; either the capsid or the foreign transgene product, in this case, GFP.

scAAV8G9-optHLA-G intrastromal injections were well tolerated with a nearly complete clearing of the cornea by 24 hours and resolution of injection-related inflammation by 3 days post-injection (FIGS. 5A-5C). These injections resulted in wide-spread corneal transduction of GFP or HLA-G isoforms in normal and injured corneas of rabbits, a species with a cornea of similar size to human corneas. Of particular note is that the injections resulted in approximately 30% corneal coverage following total injection volume of 50 μl (FIG. 5A). This volume injected intrastromally inconsistently elicited capsid neutralizing antibodies in the serum, 2 months post-injection. In contrast, no AAV vector genomes were noted in off-target tissue (e.g., liver, brain) suggesting that either the level of peripheral virus was below the sensitive detection of PCR, or AAV vector transduction was nearly entirely restricted to the cornea. Either way, and although not envisioned or anticipated, successful repeated AAV vector administration to the cornea has been reported independent of the AAV capsid vaccination (Hippert et al., *PloS One* 7:35318, (2012)).

At the therapeutic level, when compared to scAAV8G9-GFP, corneas injected with scAAV8G9-optHLA-G Combo had significantly less vascularization and inflammatory cell infiltrate 2 months following corneal injury. Correlating to other models where HLA-G suppresses angiogenesis, T cells, NK cells, B cells, and monocyte infiltrate, these data in the rabbit cornea support the notion that AAV therapy with HLA-G provides sustained immune tolerance to the ocular surface.

The results herein demonstrate the first application, to our knowledge, using AAV vectors for HLA-G gene therapy in any tissue, with optimism generated for a single dose safe and effective treatment for corneal vascularization. This effectiveness of HLA-G gene therapy in cornea has widespread implications for the treatment of ocular surface disorders in which normal immunologic tolerance is disrupted, including corneal injuries, infections, immune-mediated diseases, and prevention of corneal transplant rejection in both low and high risk patients, as well as implications for the treatment of dry eye, neovascular glaucoma, uveitis, retinal/choroid vascularization, and any solid organ transplant.

Example 2

AAV HLA-G Prevents Allogeneic Corneal Graft Rejection

Figure 12A:
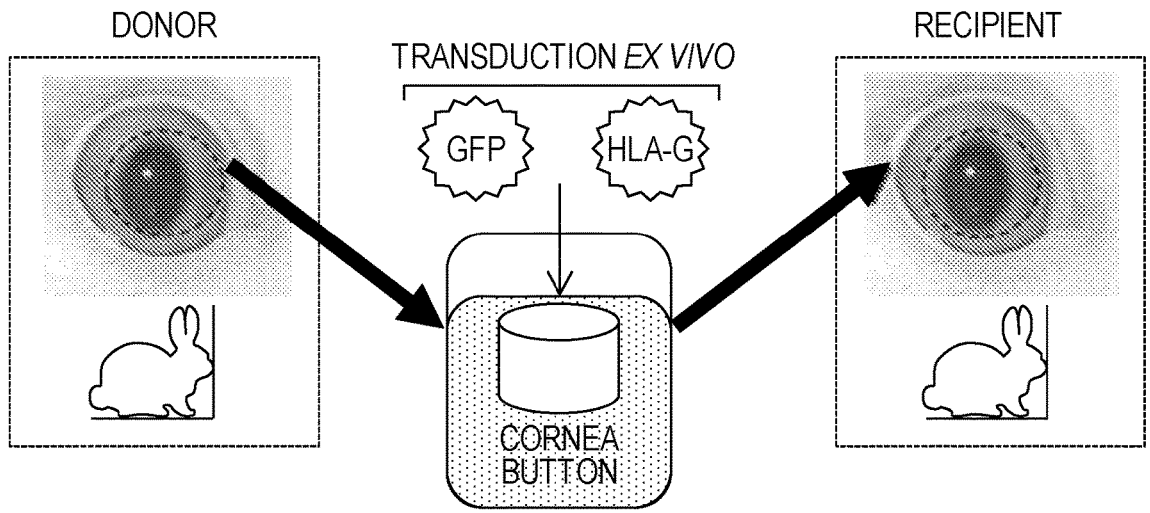
FIGS. 12A-12D show that AAV-HLA-G inhibits transplant-associated corneal immune response. A) Allogeneic corneal transplant tissues were treated ex vivo with AAV-GFP or AAV-HLA-G in rabbits. B) Corneal transplant rejection developed rapidly in eyes treated with AAV-GFP while those treated with AAV-HLA-G did not reject through day 84. C) Rejection index scores. D) Immunofluorescence showing increased HLA-G expression (red) of incubated donor tissue 84 days after surgery.
Figure 12B:
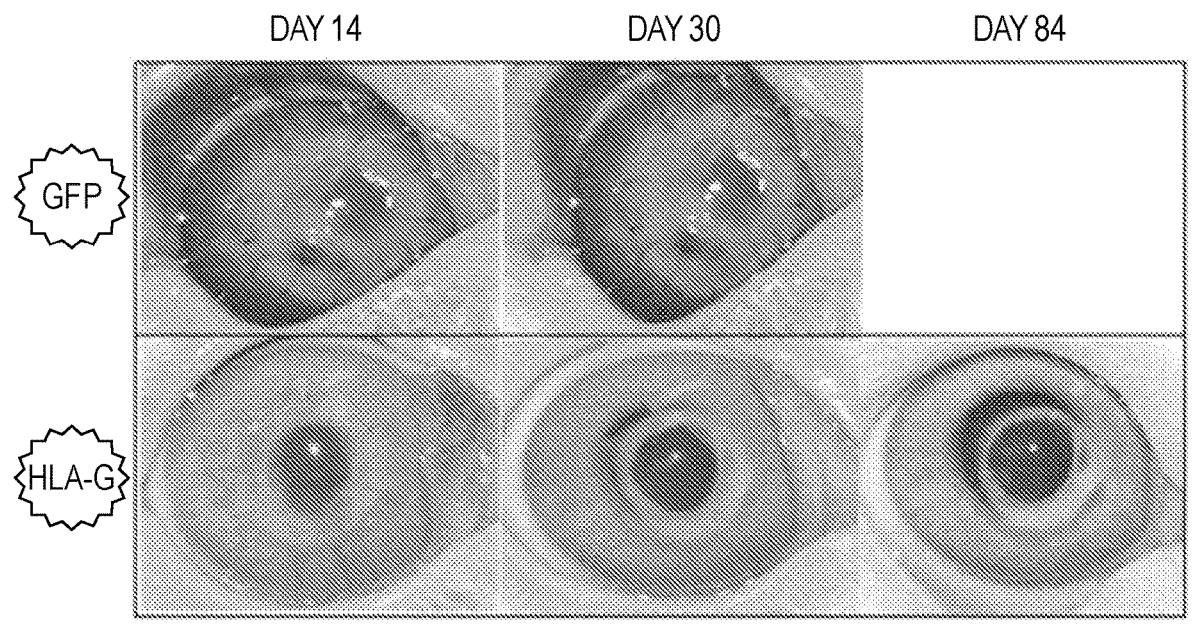
Figure 12C:
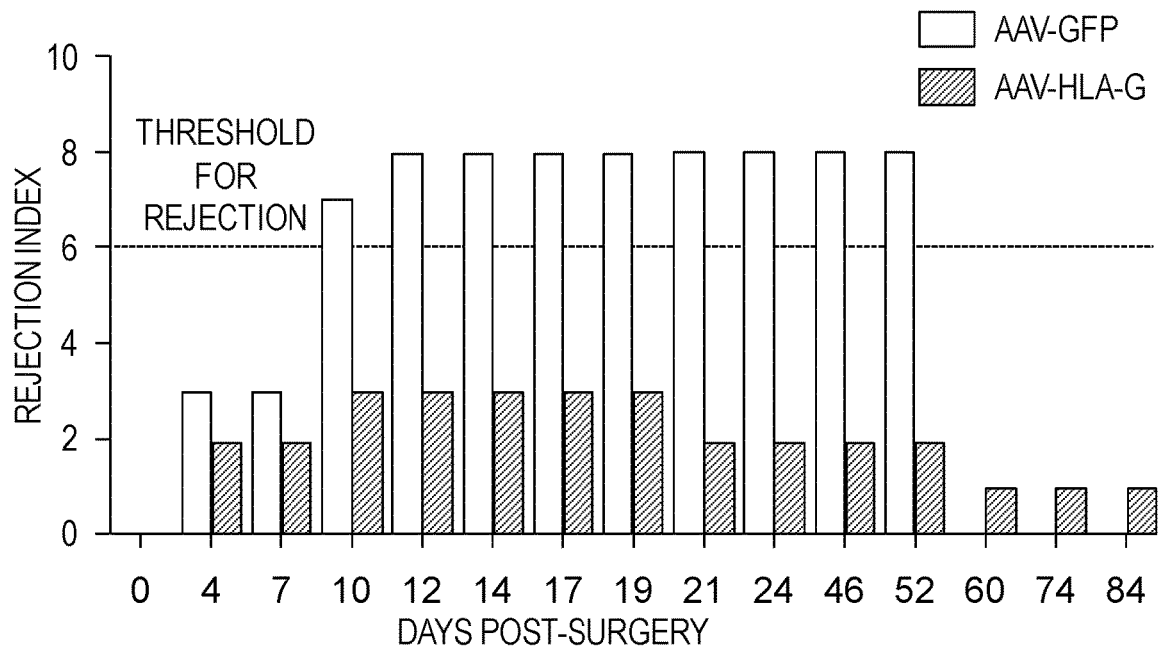
Figure 12D:
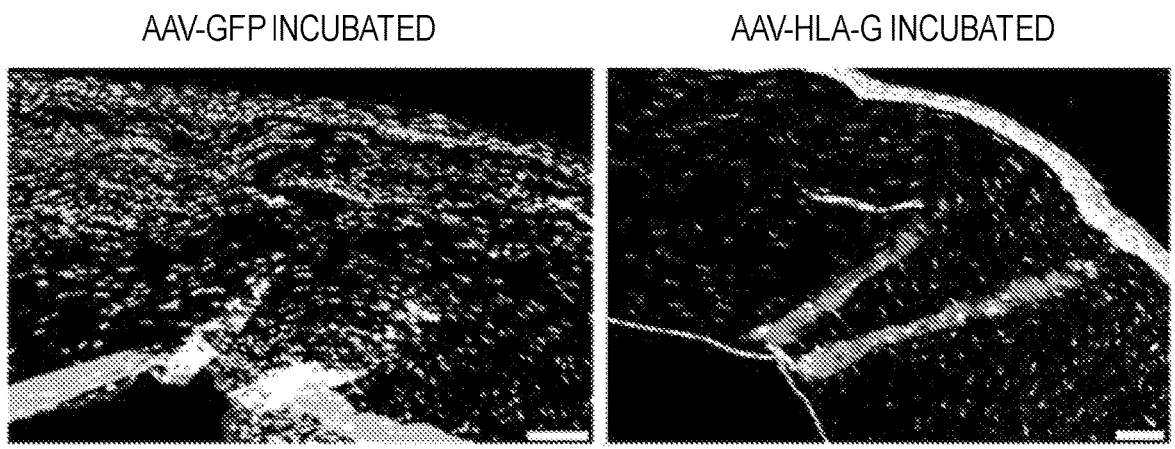

To test the ability of HLA-G to prevent graft rejection, allogeneic corneal transplantation was performed in rabbits, which are known to rapidly reject such transplants within weeks. In this experiment, a euthanized rabbit served as the cornea donor while 2 rabbits served as recipients. Prior to transplantation the corneal donor buttons were incubated in a solution containing scAAV8G9-GFP (control) or scAAV8G9-HLA-G combo for 1 hour. Corneal engraftment was monitored over time (FIGS. 12A-12D). Corneal vascularization, corneal graft edema and haze were observed in the GFP treated cornea 10 days after surgery which resulted in a rejection index (RI) greater than 6, indicating that the transplant was clinically rejected. Remarkably, the HLA-G treated corneal button remained clear with no corneal vascularization over an 84 day observation period (FIGS. 12B, 12C). In fact, the donor and recipient cornea remained completely healthy, other than a mild fibrotic surgical scar. This long-term survival of an allogeneic cornea transplant in a rabbit model demonstrates the ability for AAV-HLA-G ex vivo transduction to prevent allogeneic cornea transplant rejection and alludes to the potential for success of xenotransplantation.

The foregoing is illustrative of the present invention, and is not to be construed as limiting thereof. The invention is defined by the following claims, with equivalents of the claims to be included therein.

SEQUENCES

SEQ ID NO:1 HLA-G1 Codon Opt #1 (432)
SEQ ID NO:2 HLA-G1 Codon Opt #2 (438)
SEQ ID NO: 3 HLA-G5 (435)
SEQ ID NO:4 WT HLA-G1 (429)

That which is claimed is:

1. A polynucleotide encoding human leukocyte antigen-G (HLA-G), wherein the nucleotide sequence has been codon-optimized for expression in human cells, wherein the polynucleotide comprises the nucleotide sequence of SEQ ID NO: 1, wherein the polynucleotide provides an approximately three-fold increase in expression of HLA-G in human cells relative to the wild-type nucleotide sequence encoding HLA-G tested under otherwise identical conditions.

2. An expression cassette comprising at least one polynucleotide encoding HLA-G, wherein the at least one polynucleotide is the polynucleotide of claim 1.

3. The expression cassette of claim 2, wherein at least one of the at least one polynucleotide is operably linked to a promoter.

4. The expression cassette of claim 2, wherein at least one of the at least one polynucleotide is operably linked to a polyadenylation signal.

5. The expression cassette of claim 2, further comprising at least one adeno-associated virus (AAV) inverted terminal repeat (ITR).

6. A vector comprising the polynucleotide of claim 1.

7. The vector of claim 6, which is a viral vector.

8. The vector of claim 7, which is an AAV vector.

9. A transformed cell comprising the polynucleotide of claim 1.

10. A recombinant AAV particle comprising the polynucleotide of claim 1.

11. A pharmaceutical composition comprising the polynucleotide of claim 1 and a pharmaceutically acceptable carrier.

12. A method of expressing HLA-G in a cell, comprising contacting the cell with the recombinant AAV particle of claim 10, thereby expressing HLA-G in the cell.

13. A method of delivering HLA-G to a cornea explant, comprising contacting the cornea explant with the recombinant AAV particle of claim 10, thereby delivering HLA-G to the cornea explant.

14. A method of inhibiting rejection of a cornea explant after transplantation in a mammalian subject, comprising contacting the cornea explant with the recombinant AAV particle of claim 10, thereby inhibiting rejection of the cornea explant after transplantation.

15. A method of administering HLA-G to the eye of a mammalian subject, comprising administering to the eye of the mammalian subject a cell that has been contacted with the recombinant AAV particle of claim 10, thereby administering HLA-G to the eye of the mammalian subject.

16. A method of administering HLA-G to the eye of a mammalian subject, comprising administering to the eye of the mammalian subject the recombinant AAV particle of claim 10, thereby administering HLA-G to the eye of the mammalian subject.

17. A polynucleotide encoding human leukocyte antigen-G (HLA-G), wherein the nucleotide sequence has been codon-optimized for expression in human cells, wherein the polynucleotide comprises a nucleotide sequence at least 95% identical to SEQ ID NO: 2.

18. The polynucleotide of claim 17, wherein the polynucleotide comprises the nucleotide sequence of SEQ ID NO: 2.

* * * * *

UNITED STATES PATENT AND TRADEMARK OFFICE
CERTIFICATE OF CORRECTION

PATENT NO. : 11,866,480 B2
APPLICATION NO. : 16/318070
DATED : January 9, 2024
INVENTOR(S) : Hirsch et al.

Page 1 of 1

It is certified that error appears in the above-identified patent and that said Letters Patent is hereby corrected as shown below:

On the Title Page

(56) References Cited, OTHER PUBLICATIONS, Page 2, Column 1, Lines 8-9: Please correct "Vance et ai. "AAV Gene Therapy for MPS1-associated Corneal Blindness", Scientific Reports 6(1):1-10 (2016)" to read --Vance et al. "AAV Gene Therapy for MPS1-associated Corneal Blindness", Scientific Reports 6(1):1-10 (2016)--

(56) References Cited, OTHER PUBLICATIONS, Page 2, Column 2, Lines 10-11: Please correct "Full English of Office Action corresponding to Chinese Application No. 201780049218.8 issued July 28, 2023" to read --Full English translation of Office Action corresponding to Chinese Application No. 201780049218.8 issued July 28, 2023--

In the Specification

Column 6, Line 24: Please correct "*Patent In*" to read --*PatentIn*--

Column 28, Line 51: Please correct "12.50." to read --12.5 µl.--

Signed and Sealed this
Ninth Day of April, 2024

Katherine Kelly Vidal
*Director of the United States Patent and Trademark Office*